(12) United States Patent
Jiménez et al.

US008067577B2

(10) Patent No.: US 8,067,577 B2
(45) Date of Patent: Nov. 29, 2011

(54) METHODS AND COMPOSITIONS FOR THE TREATMENT OF INTESTINAL CONDITIONS

(75) Inventors: Ana I. Jiménez, Madrid (ES); Irene Gascón, Madrid (ES); Maria Concepción Jiménez, Madrid (ES); José P. Román, Madrid (ES); Angela Sesto, Madrid (ES)

(73) Assignee: Sylentis S.A.U. (ES)

( * ) Notice: Subject to any disclaimer, the term of this patent is extended or adjusted under 35 U.S.C. 154(b) by 0 days.

(21) Appl. No.: 12/871,366

(22) Filed: Aug. 30, 2010

(65) Prior Publication Data

US 2010/0317720 A1 Dec. 16, 2010

Related U.S. Application Data

(60) Division of application No. 11/858,579, filed on Sep. 20, 2007, now Pat. No. 7,807,650, which is a continuation-in-part of application No. PCT/GB2006/050051, filed on Mar. 14, 2006.

(30) Foreign Application Priority Data

Mar. 14, 2005 (GB) .................................. 0505081.0

(51) Int. Cl.
*C07H 21/04* (2006.01)
*A61K 31/70* (2006.01)

(52) U.S. Cl. ........................................ 536/24.5; 514/44

(58) Field of Classification Search ........................ None
See application file for complete search history.

(56) References Cited

U.S. PATENT DOCUMENTS

| 7,176,304 B2 | 2/2007 | McSwiggen et al. | |
|---|---|---|---|
| 2003/0108923 A1 * | 6/2003 | Tuschl et al. | 435/6 |
| 2004/0115641 A1 | 6/2004 | Cowsert et al. | |
| 2004/0241843 A1 | 12/2004 | Baker et al. | |
| 2005/0013854 A1 | 1/2005 | Mannino et al. | |
| 2005/0026278 A1 | 2/2005 | Tuschl et al. | |
| 2005/0272682 A1 | 12/2005 | Evers et al. | |
| 2006/0172963 A1 | 8/2006 | Shepard et al. | |
| 2006/0172965 A1 | 8/2006 | Shepard et al. | |
| 2007/0249549 A1 | 10/2007 | Axelsson et al. | |

FOREIGN PATENT DOCUMENTS

| GB | 2406568 | 4/2005 |
|---|---|---|
| WO | WO 03/070744 | 8/2003 |
| WO | WO 2004/029212 | 4/2004 |
| WO | WO 2004/042024 | 5/2004 |
| WO | WO 2004/045543 | 6/2004 |
| WO | WO 2004/091572 | 10/2004 |
| WO | WO 2005/044976 | 5/2005 |
| WO | WO 2005/045037 | 5/2005 |

OTHER PUBLICATIONS

Akashi et al., "Suppression of Gene Expression by RNA Interference in Cultured Plant Cells," Antisense Nucleic Acid Drug Dev, 2001, 11(6):359-367.

Ambion, Tech Notes 10(4) and siRNA Target Finder (http://www.ambion.com/techlib/misc/siRNA_finder.html, available to the public) retrieved on May 1, 2008, siRNA target hit for SEQ ID No. 139 included.
Banerjee et al., "Control of Developmental Timing by Small Temporal RNAs: a Paradigm for RNA-mediated Regulation of Gene Expression," Bioessays, 2002, 24(2):119-129.
Bass, "The Short Answer," Nature, vol. 411, pp. 428-429, 2001.
Borg et al., "NK Cell Activation by Dendritic Cells (DCs) Requires the Formation of a Synapse Leading to IL-12 Polarization in DCs," Blood, Nov. 15, 2004, 104(10):3267-3275.
Bosher et al., "RNA Interference: Genetic Wand and Genetic Watchdog," Nat Cell Biol, 2000, 2(2):E31-6.
Braasch et al., "Novel Antisense and Peptide Nucleic Acid Strategies for Controlling Gene Expression," Biochemistry, 2002, 41(14):4503-4510.
Brummelkamp et al., "A System for Stable Expression of Short Interfering RNAs in Mammalian Cells," Science, American Association for the Advancement of Science, 2002, 296(5567):550-553.
Caplen et al., "Specific inhibition of Gene Expression by Small Double Stranded RNAs in Invertebrate and Vertebrate Systems," Proc. Natl. Acad. Sci. USA, 2001,98: 9742-9747.
Caspi, "Short Analytical Review IL-12 in Autoimmnuity," Clinical Immunology and Immunopathology, Jul. 1998, 88(1):4-13.
Davidson et al, "IL-12, But Not IFN-γ, Plays a Major Role in Sustaining the Chronic Phase of Colitis in IL-10-Deficient Mice," The Journal of Immunology, 1998, pp. 3144-3149.
Denkert et al., "Induction of G0/G1 Cell Cycle Arrest in Ovarian Carcinoma Cells by the Ant-Inflammatory Drug NS-398, but not by COX-2-Specific RNA Interference," Oncogene, 2003, 22:8653-8661.
Elabashir et al., "Duplexes of 21-Nucleotide RNAs mediate RNA interference in Cultured Mammalian Cells," Nature, May 24, 2001, 411(6836):494-498.
Elbashir et al., "RNA Interference is Mediated by 21- and 22-Nucleotide RNAs," Genes Dev, 2001, 15(2)188-200.
Fais et al., "Interferon Expression in Crohn's Disease Patients: Increased Interferon-γ and -α mRNA in the Intestinal Lamina Propria Mononuclear Cells," Journal of Interferon Research, 1994, 14:235-238.
Fire et al., "Potent and Specific Genetic Interference by Double Stranded RNA in a *Caenorhabditis elegans*," Nature, 1998, 391(6669):806-11.
Flynn et al., "Efficient Delivery of Small Interfering RNA for Inhibition of IL-12p40 Expression in vivo," Journal of Inflammation, 2004, 1(4):1-12.
Fuss et al., "Disparate CD4 Lamina Propria (LP) Lymphokine Secretion Profiles in Inflammatory Bowel Disease," The Journal of Immunology, 1996, pp. 1261-1270.
Gately et al., "The Interleukin-12/Interleukin-12-Receptor System: Role in Normal and Pathologic Immune Responses," Annual Review of Immunology, 1998, 16:495-521.
Ge et al., "RNA Interference of Influenza Virus Production by Directly Targeting mRNA for Degradation and Indirectly Inhibiting all Viral RNA Transcription," Proc Natl Acad Sci USA., 2003, 100(5):2718-2723.

(Continued)

*Primary Examiner* — Tracy Vivlemore
(74) *Attorney, Agent, or Firm* — Margaret B. Brivanlou; Kenneth H. Sonnenfeld; King & Spalding LLP

(57) ABSTRACT

Methods and compositions for the treatment of intestinal disorders, such as IBD and Crohn's disease, are disclosed. Preferred compositions include siNA. Also disclosed is a method of specifically targeting siNA to treat intestinal disorders by intrarectal administration of siNA compounds.

11 Claims, 22 Drawing Sheets

OTHER PUBLICATIONS

Gersemann et al., "Crohn's Disease-Defect in Innate Defence," World J. Gastroenerol., 14(36), pp. 5499-5503, 2008.

Gil et al., "Induction of Apoptosis by the dsRNA-dependent Protein Kinase (PKR): Mechanism of Action," Apoptosis, 2000, 5(2):107-114.

Grosshans et al., "Micro-RNAs: Small is Plentiful," J Cell Biol, 2002, 156(1):17-21.

Hammond et al., "Post-Transcriptional Gene Silencing By Double-Standed RNA," Nature, 2001, 2:110-119.

Hill et al., "Immune Modulation by Silencing IL-12 Production in Dendritic Cells Using Small Interfering RNA," The Journal of Immunology, 2003, 171:691-696.

Jackson et al., "Targeted RNA Interference of P13K Pathway Components Confers with Survival Benefit in a Mouse Model of Inflammatory Bowel Disease," Journal of the American College of Surgeons, vol. 201, p. S15, Sep. 2005.

Krutzfeldt et al., "Silencing of microRNAs in vivo with 'Antagomirs'," Nature, 2005, 438(7068):685-689.

Mahato et al., "Modulation of Gene Expression by Antisense and Antigene Oligodeoxynucleotides and Small Interfering RNA," Expert Opinion on Drug Delivery, Jan. 2005, 2(1):3-28.

Mannon et al., "Anti-Interleukin-12 Antibody for Active Crohn's Disease," The New England Journal of Medicine, Nov. 11, 2004, 351(20):2069-2080.

Miller et al., "Allele-specific Silencing of Dominant Disease Genes," Proceedings of the National Academy of Sciences of USA, Jun. 10, 2003, 100(12):7195-7200.

Monteleone et al., Interleukin 12 Is Expressed and Actively Released by Crohn's Disease Intestinal Lamina Propria Mononuclear Cells, Gastroenterology, 1997, 112:1169-1178.

Neurath et al., "Antibodies to Interleukin 12 Abrogate Established Experimental Colitis in Mice," The Journal of Experimental Medicine, Nov. 1995, 182:1281-1290.

Paddison et al., "Short hairpin RNAs (shRNAs) Induce Sequence-Specific Silencing in Mammalian Cells," Genes Dev, 2002, 16(8):948-958.

Parronchi et al., "Type 1 T-Helper Cell Predominance and Interleukin-12 Expression in the Gut of Patients with Crohn's Disease," American Journal of Pathology, Mar. 1997, 150(3):823-832.

Plevy et al., "A Role for TNF-α and Mucosal T Helper-1 Cytokines in the Pathogenesis of Crohn's Disease," The Journal of Immunology, 1997, 6276-6282.

Rogler, et al., "Cytokines in Inflammatory Bowel Disease," World Journal of Surgery, vol. 22, pp. 382-389, 1998.

Scherer et al., "Approaches for the Sequence-Specific Knockdown of mRNA," Nat. Biotechnology, 2003, 21(12):1457-1465.

Simpson et al., "T Cell-mediated Pathology in Two Models of Experimental Colitis Depends Predominantly on the Interleukin 12/Signal Transducer and Activator of Transcription (Stat)-4 Pathway, but Is Not Conditional on Interferon γ Expression T Cells," J. Exp. Med., Apr. 20, 1998, 187(8):1225-1234.

Trinchieri, "Interleukin-12: A Cytokine at the Interface of Inflammation and Immunity," Advances in Immunology, 1998, 70:83-243.

Tuschl et al., "Targeted mRNA degradation by double-stranded RNA in vitro," Genes Dev., 1999, 13(24):3191-3197.

Uprichard et al., The Therapeutic Potential of RNA Interference, FEBS Letters, Oct. 31, 2005 579(26):5996-6007.

Vandenbroeck et al., "Inhibiting Cytokines of the Interleukin-12 Family: Recent Advances and Novel Challenges," Journal of Pharmacy and Pharmacology, 2004, 56:145-160.

Wetering et al., "Specific Inhibition of Gene Expression Using a Stably Integrated, Inducible Small-Interfering-RNA Vector," EMBO Reports, Jun. 2003, 4(6):609-615.

Wianny et al., "Specific Interference with Gene Function by Double-Stranded RNA in Early Mouse Development," Nat Cell Biol, 2000, 2(2):70-75.

Williams BR, "Role of the Double-Stranded RNA-activated Protein kinase (PKR) in Cell Regulation," Biochem Soc Trans, 1997, 25(2):509-513.

Wiznerowicz et al., "Conditional Suppression of Cellular Genes: Lentivirus Vector-Mediated Drug-Inducible RNA Interference," Journal of Virology, Aug. 2003, 77(16):8957-8961.

Xie et al., "Harnessing in vivo siRNA Delivery for Drug Discovery and Therapeutic Development," Drug Discovery Today, Jan. 2006, 11(1-2):67-73.

* cited by examiner

Fig. 1A

| | |
|---|---|
| SEQ ID NO: 1 | 5' UGUUCCCAUGCCUUCACCA 3'<br>\|\|\|\|\|\|\|\|\|\|\|\|\|\|\|\|\|\| |
| SEQ ID NO: 97 | 3' ACAAGGGUACGGAAGUGGU 5' |
| SEQ ID NO: 2 | 5' AACCUGCUGAGGGCCGUCA 3'<br>\|\|\|\|\|\|\|\|\|\|\|\|\|\|\|\|\|\| |
| SEQ ID NO: 98 | 3' UUGGACGACUCCCGGCAGU 5' |
| SEQ ID NO: 3 | 5' CAUGCUCCAGAAGGCCAGA 3'<br>\|\|\|\|\|\|\|\|\|\|\|\|\|\|\|\|\|\| |
| SEQ ID NO: 99 | 3' GUACGAGGUCUUCCGGUCU 5' |
| SEQ ID NO: 4 | 5' GGCCAGACAAACUCUAGAA 3'<br>\|\|\|\|\|\|\|\|\|\|\|\|\|\|\|\|\|\| |
| SEQ ID NO: 100 | 3' CCGGUCUGUUUGAGAUCUU 5' |
| SEQ ID NO: 5 | 5' AACCAGCACAGUGGAGGCC 3'<br>\|\|\|\|\|\|\|\|\|\|\|\|\|\|\|\|\|\| |
| SEQ ID NO: 101 | 3' UUGGUCGUGUCACCUCCGG 5' |
| SEQ ID NO: 6 | 5' ACCAGCACAGUGGAGGCCU 3'<br>\|\|\|\|\|\|\|\|\|\|\|\|\|\|\|\|\|\| |
| SEQ ID NO: 102 | 3' UGGUCGUGUCACCUCCGGA 5' |
| SEQ ID NO: 7 | 5' CCAAGAAUGAGAGUUGCCU 3'<br>\|\|\|\|\|\|\|\|\|\|\|\|\|\|\|\|\|\| |
| SEQ ID NO: 103 | 3' GGUUCUUACUCUCAACGGA 5' |
| SEQ ID NO: 8 | 5' GAAUGAGAGUUGCCUAAAU 3'<br>\|\|\|\|\|\|\|\|\|\|\|\|\|\|\|\|\|\| |
| SEQ ID NO: 104 | 3' CUUACUCUCAACGGAUUUA 5' |
| SEQ ID NO: 9 | 5' UGAGAGUUGCCUAAAUUCC 3'<br>\|\|\|\|\|\|\|\|\|\|\|\|\|\|\|\|\|\| |
| SEQ ID NO: 105 | 3' ACUCUCAACGGAUUUAAGG 5' |
| SEQ ID NO: 10 | 5' AUUCCAGAGAGACCUCUUU 3'<br>\|\|\|\|\|\|\|\|\|\|\|\|\|\|\|\|\|\| |
| SEQ ID NO: 106 | 3' UAAGGUCUCUCUGGAGAAA 5' |
| SEQ ID NO: 11 | 5' UUCCAGAGAGACCUCUUUC 3'<br>\|\|\|\|\|\|\|\|\|\|\|\|\|\|\|\|\|\| |
| SEQ ID NO: 107 | 3' AAGGUCUCUCUGGAGAAAG 5' |
| SEQ ID NO: 12 | 5' CUAAUGGGAGUUGCCUGGC 3'<br>\|\|\|\|\|\|\|\|\|\|\|\|\|\|\|\|\|\| |
| SEQ ID NO: 108 | 3' GAUUACCCUCAACGGACCG 5' |
| SEQ ID NO: 13 | 5' GACUUGAAGAUGUACCAGG 3'<br>\|\|\|\|\|\|\|\|\|\|\|\|\|\|\|\|\|\| |
| SEQ ID NO: 109 | 3' CUGAACUUCUACAUGGUCC 5' |
| SEQ ID NO: 14 | 5' GAUGUACCAGGUGGAGUUC 3'<br>\|\|\|\|\|\|\|\|\|\|\|\|\|\|\|\|\|\| |
| SEQ ID NO: 110 | 3' CUACAUGGUCCACCUCAAG 5' |
| SEQ ID NO: 15 | 5' GACCAUGAAUGCAAAGCUU 3'<br>\|\|\|\|\|\|\|\|\|\|\|\|\|\|\|\|\|\| |
| SEQ ID NO: 111 | 3' CUGGUACUUACGUUUCGAA 5' |
| SEQ ID NO: 16 | 5' UGCAAAGCUUCUGAUGGAU 3'<br>\|\|\|\|\|\|\|\|\|\|\|\|\|\|\|\|\|\| |
| SEQ ID NO: 112 | 3' ACGUUUCGAAGACUACCUA 5' |
| SEQ ID NO: 17 | 5' AGCUUCUGAUGGAUCCUAA 3'<br>\|\|\|\|\|\|\|\|\|\|\|\|\|\|\|\|\|\| |
| SEQ ID NO: 113 | 3' UCGAAGACUACCUAGGAUU 5' |
| SEQ ID NO: 18 | 5' GCUUCUGAUGGAUCCUAAG 3'<br>\|\|\|\|\|\|\|\|\|\|\|\|\|\|\|\|\|\| |
| SEQ ID NO: 114 | 3' CGAAGACUACCUAGGAUUC 5' |
| SEQ ID NO: 19 | 5' GAGGCAGAUCUUUCUAGAU 3'<br>\|\|\|\|\|\|\|\|\|\|\|\|\|\|\|\|\|\| |
| SEQ ID NO: 115 | 3' CUCCGUCUAGAAAGAUCUA 5' |
| SEQ ID NO: 20 | 5' AACAUGCUGGCAGUUAUUG 3'<br>\|\|\|\|\|\|\|\|\|\|\|\|\|\|\|\|\|\| |
| SEQ ID NO: 116 | 3' UUGUACGACCGUCAAUAAC 5' |
| SEQ ID NO: 21 | 5' ACAUGCUGGCAGUUAUUGA 3'<br>\|\|\|\|\|\|\|\|\|\|\|\|\|\|\|\|\|\| |
| SEQ ID NO: 117 | 3' UGUACGACCGUCAAUAACU 5' |

Fig. 1B

| SEQ ID NO: 22 | 5' CAUGCUGGCAGUUAUUGAU 3' |
| --- | --- |
| | ‖‖‖‖‖‖‖‖‖‖‖‖‖‖‖‖‖‖ |
| SEQ ID NO: 118 | 3' GUACGACCGUCAAUAACUA 5' |
| SEQ ID NO: 23 | 5' UUUCAACAGUGAGACUGUG 3' |
| | ‖‖‖‖‖‖‖‖‖‖‖‖‖‖‖‖‖‖ |
| SEQ ID NO: 119 | 3' AAAGUUGUCACUCUGACAC 5' |
| SEQ ID NO: 24 | 5' CAGUGAGACUGUGCCACAA 3' |
| | ‖‖‖‖‖‖‖‖‖‖‖‖‖‖‖‖‖‖ |
| SEQ ID NO: 120 | 3' GUCACUCUGACACGGUGUU 5' |
| SEQ ID NO: 25 | 5' AAAUCCUCCCUUGAAGAAC 3' |
| | ‖‖‖‖‖‖‖‖‖‖‖‖‖‖‖‖‖‖ |
| SEQ ID NO: 121 | 3' UUUAGGAGGGAACUUCUUG 5' |
| SEQ ID NO: 26 | 5' AAUCCUCCCUUGAAGAACC 3' |
| | ‖‖‖‖‖‖‖‖‖‖‖‖‖‖‖‖‖‖ |
| SEQ ID NO: 122 | 3' UUAGGAGGGAACUUCUUGG 5' |
| SEQ ID NO: 27 | 5' AUCCUCCCUUGAAGAACCG 3' |
| | ‖‖‖‖‖‖‖‖‖‖‖‖‖‖‖‖‖‖ |
| SEQ ID NO: 123 | 3' UAGGAGGGAACUUCUUGGC 5' |
| SEQ ID NO: 28 | 5' UCCUCCCUUGAAGAACCGG 3' |
| | ‖‖‖‖‖‖‖‖‖‖‖‖‖‖‖‖‖‖ |
| SEQ ID NO: 124 | 3' AGGAGGGAACUUCUUGGCC 5' |
| SEQ ID NO: 29 | 5' AAUCAAGCUCUGCAUACUU 3' |
| | ‖‖‖‖‖‖‖‖‖‖‖‖‖‖‖‖‖‖ |
| SEQ ID NO: 125 | 3' UUAGUUCGAGACGUAUGAA 5' |
| SEQ ID NO: 30 | 5' AUCAAGCUCUGCAUACUUC 3' |
| | ‖‖‖‖‖‖‖‖‖‖‖‖‖‖‖‖‖‖ |
| SEQ ID NO: 126 | 3' UAGUUCGAGACGUAUGAAG 5' |
| SEQ ID NO: 31 | 5' UCAAGCUCUGCAUACUUCU 3' |
| | ‖‖‖‖‖‖‖‖‖‖‖‖‖‖‖‖‖‖ |
| SEQ ID NO: 127 | 3' AGUUCGAGACGUAUGAAGA 5' |
| SEQ ID NO: 32 | 5' GCUCUGCAUACUUCUUCAU 3' |
| | ‖‖‖‖‖‖‖‖‖‖‖‖‖‖‖‖‖‖ |
| SEQ ID NO: 128 | 3' CGAGACGUAUGAAGAAGUA 5' |
| SEQ ID NO: 33 | 5' UUCGGGCAGUGACUAUUGA 3' |
| | ‖‖‖‖‖‖‖‖‖‖‖‖‖‖‖‖‖‖ |
| SEQ ID NO: 129 | 3' AAGCCCGUCACUGAUAACU 5' |

| SEQ ID NO: 34 | 5' UUGGAUUGGUAUCCGGAUG 3' |
| --- | --- |
| | ‖‖‖‖‖‖‖‖‖‖‖‖‖‖‖‖‖‖ |
| SEQ ID NO: 130 | 3' AACCUAACCAUAGGCCUAC 5' |
| SEQ ID NO: 35 | 5' AUGGUGGUCCUCACCUGUG 3' |
| | ‖‖‖‖‖‖‖‖‖‖‖‖‖‖‖‖‖‖ |
| SEQ ID NO: 131 | 3' UACCACCAGGAGUGGACAC 5' |
| SEQ ID NO: 36 | 5' UGGUGGUCCUCACCUGUGA 3' |
| | ‖‖‖‖‖‖‖‖‖‖‖‖‖‖‖‖‖‖ |
| SEQ ID NO: 132 | 3' ACCACCAGGAGUGGACACU 5' |
| SEQ ID NO: 37 | 5' GAAGAUGGUAUCACCUGGA 3' |
| | ‖‖‖‖‖‖‖‖‖‖‖‖‖‖‖‖‖‖ |
| SEQ ID NO: 133 | 3' CUUCUACCAUAGUGGACCU 5' |
| SEQ ID NO: 38 | 5' GAUGGUAUCACCUGGACCU 3' |
| | ‖‖‖‖‖‖‖‖‖‖‖‖‖‖‖‖‖‖ |
| SEQ ID NO: 134 | 3' CUACCAUAGUGGACCUGGA 5' |
| SEQ ID NO: 39 | 5' AACCCUGACCAUCCAAGUC 3' |
| | ‖‖‖‖‖‖‖‖‖‖‖‖‖‖‖‖‖‖ |
| SEQ ID NO: 135 | 3' UUGGGACUGGUAGGUUCAG 5' |
| SEQ ID NO: 40 | 5' ACCCUGACCAUCCAAGUCA 3' |
| | ‖‖‖‖‖‖‖‖‖‖‖‖‖‖‖‖‖‖ |
| SEQ ID NO: 136 | 3' UGGGACUGGUAGGUUCAGU 5' |
| SEQ ID NO: 41 | 5' CCCUGACCAUCCAAGUCAA 3' |
| | ‖‖‖‖‖‖‖‖‖‖‖‖‖‖‖‖‖‖ |
| SEQ ID NO: 137 | 3' GGGACUGGUAGGUUCAGUU 5' |
| SEQ ID NO: 42 | 5' GUCAAAGAGUUUGGAGAUG 3' |
| | ‖‖‖‖‖‖‖‖‖‖‖‖‖‖‖‖‖‖ |
| SEQ ID NO: 138 | 3' CAGUUUCUCAAACCUCUAC 5' |

Fig. 1C

| | |
|---|---|
| SEQ ID NO: 43 | 5' AGAGUUUGGAGAUGCUGGC 3'<br>\|\|\|\|\|\|\|\|\|\|\|\|\|\|\|\|\|\|\| |
| SEQ ID NO: 139 | 3' UCUCAAACCUCUACGACCG 5' |
| SEQ ID NO: 44 | 5' GAGUUUGGAGAUGCUGGCC 3'<br>\|\|\|\|\|\|\|\|\|\|\|\|\|\|\|\|\|\|\| |
| SEQ ID NO: 140 | 3' CUCAAACCUCUACGACCGG 5' |
| SEQ ID NO: 45 | 5' AGGAGGCGAGGUUCUAAGC 3'<br>\|\|\|\|\|\|\|\|\|\|\|\|\|\|\|\|\|\|\| |
| SEQ ID NO: 141 | 3' UCCUCCGCUCCAAGAUUCG 5' |
| SEQ ID NO: 46 | 5' GGAGGCGAGGUUCUAAGCC 3'<br>\|\|\|\|\|\|\|\|\|\|\|\|\|\|\|\|\|\|\| |
| SEQ ID NO: 142 | 3' CCUCCGCUCCAAGAUUCGG 5' |
| SEQ ID NO: 47 | 5' GCCAUUCGCUCCUGCUGCU 3'<br>\|\|\|\|\|\|\|\|\|\|\|\|\|\|\|\|\|\|\| |
| SEQ ID NO: 143 | 3' CGGUAAGCGAGGACGACGA 5' |
| SEQ ID NO: 48 | 5' AAAGGAAGAUGGAAUUUGG 3'<br>\|\|\|\|\|\|\|\|\|\|\|\|\|\|\|\|\|\|\| |
| SEQ ID NO: 144 | 3' UUUCCUUCUACCUUAAACC 5' |
| SEQ ID NO: 49 | 5' AAGGAAGAUGGAAUUUGGU 3'<br>\|\|\|\|\|\|\|\|\|\|\|\|\|\|\|\|\|\|\| |
| SEQ ID NO: 145 | 3' UUCCUUCUACCUUAAACCA 5' |
| SEQ ID NO: 50 | 5' AGGAAGAUGGAAUUUGGUC 3'<br>\|\|\|\|\|\|\|\|\|\|\|\|\|\|\|\|\|\|\| |
| SEQ ID NO: 146 | 3' UCCUUCUACCUUAAACCAG 5' |
| SEQ ID NO: 51 | 5' GGAAGAUGGAAUUUGGUCC 3'<br>\|\|\|\|\|\|\|\|\|\|\|\|\|\|\|\|\|\|\| |
| SEQ ID NO: 147 | 3' CCUUCUACCUUAAACCAGG 5' |
| SEQ ID NO: 52 | 5' GAUGGAAUUUGGUCCACUG 3'<br>\|\|\|\|\|\|\|\|\|\|\|\|\|\|\|\|\|\|\| |
| SEQ ID NO: 148 | 3' CUACCUUAAACCAGGUGAC 5' |
| SEQ ID NO: 53 | 5' AGGACCAGAAAGAACCCAA 3'<br>\|\|\|\|\|\|\|\|\|\|\|\|\|\|\|\|\|\|\| |
| SEQ ID NO: 149 | 3' UCCUGGUCUUUCUUGGGUU 5' |
| SEQ ID NO: 54 | 5' GGACCAGAAAGAACCCAAA 3'<br>\|\|\|\|\|\|\|\|\|\|\|\|\|\|\|\|\|\|\| |
| SEQ ID NO: 150 | 3' CCUGGUCUUUCUUGGGUUU 5' |
| SEQ ID NO: 55 | 5' UAAGACCUUUCUAAGAUGC 3'<br>\|\|\|\|\|\|\|\|\|\|\|\|\|\|\|\|\|\|\| |
| SEQ ID NO: 151 | 3' AUUCUGGAAAGAUUCUACG 5' |
| SEQ ID NO: 56 | 5' GACCUUUCUAAGAUGCGAG 3'<br>\|\|\|\|\|\|\|\|\|\|\|\|\|\|\|\|\|\|\| |
| SEQ ID NO: 152 | 3' CUGGAAAGAUUCUACGCUC 5' |
| SEQ ID NO: 57 | 5' GAUGCGAGGCCAAGAAUUA 3'<br>\|\|\|\|\|\|\|\|\|\|\|\|\|\|\|\|\|\|\| |
| SEQ ID NO: 153 | 3' CUACGCUCCGGUUCUUAAU 5' |
| SEQ ID NO: 58 | 5' GAAUUAUUCUGGACGUUUC 3'<br>\|\|\|\|\|\|\|\|\|\|\|\|\|\|\|\|\|\|\| |
| SEQ ID NO: 154 | 3' CUUAAUAAGACCUGCAAAG 5' |
| SEQ ID NO: 59 | 5' UUAUUCUGGACGUUUCACC 3'<br>\|\|\|\|\|\|\|\|\|\|\|\|\|\|\|\|\|\|\| |
| SEQ ID NO: 155 | 3' AAUAAGACCUGCAAAGUGG 5' |
| SEQ ID NO: 60 | 5' AAGCAGCAGAGGCUCUUCU 3'<br>\|\|\|\|\|\|\|\|\|\|\|\|\|\|\|\|\|\|\| |
| SEQ ID NO: 156 | 3' UUCGUCGUCUCCGAGAAGA 5' |
| SEQ ID NO: 61 | 5' AGCAGCAGAGGCUCUUCUG 3'<br>\|\|\|\|\|\|\|\|\|\|\|\|\|\|\|\|\|\|\| |
| SEQ ID NO: 157 | 3' UCGUCGUCUCCGAGAAGAC 5' |
| SEQ ID NO: 62 | 5' GCAGCAGAGGCUCUUCUGA 3'<br>\|\|\|\|\|\|\|\|\|\|\|\|\|\|\|\|\|\|\| |
| SEQ ID NO: 158 | 3' CGUCGUCUCCGAGAAGACU 5' |
| SEQ ID NO: 63 | 5' CAAGGAGUAUGAGUACUCA 3'<br>\|\|\|\|\|\|\|\|\|\|\|\|\|\|\|\|\|\|\| |
| SEQ ID NO: 159 | 3' GUUCCUCAUACUCAUGAGU 5' |
| SEQ ID NO: 64 | 5' GGAGUAUGAGUACUCAGUG 3'<br>\|\|\|\|\|\|\|\|\|\|\|\|\|\|\|\|\|\|\| |
| SEQ ID NO: 160 | 3' CCUCAUACUCAUGAGUCAC 5' |

Fig. 1D

| SEQ ID NO: 65 | 5' AACUACACCAGCAGCUUCU 3' |
| | \|\|\|\|\|\|\|\|\|\|\|\|\|\|\|\|\|\|\| |
| SEQ ID NO: 161 | 3' UUGAUGUGGUCGUCGAAGA 5' |
| SEQ ID NO: 66 | 5' ACUACACCAGCAGCUUCUU 3' |
| | \|\|\|\|\|\|\|\|\|\|\|\|\|\|\|\|\|\|\| |
| SEQ ID NO: 162 | 3' UGAUGUGGUCGUCGAAGAA 5' |
| SEQ ID NO: 67 | 5' CUACACCAGCAGCUUCUUC 3' |
| | \|\|\|\|\|\|\|\|\|\|\|\|\|\|\|\|\|\|\| |
| SEQ ID NO: 163 | 3' GAUGUGGUCGUCGAAGAAG 5' |
| SEQ ID NO: 68 | 5' ACCUGACCCACCCAAGAAC 3' |
| | \|\|\|\|\|\|\|\|\|\|\|\|\|\|\|\|\|\|\| |
| SEQ ID NO: 164 | 3' UGGACUGGGUGGGUUCUUG 5' |
| SEQ ID NO: 69 | 5' CCUGACCCACCCAAGAACU 3' |
| | \|\|\|\|\|\|\|\|\|\|\|\|\|\|\|\|\|\|\| |
| SEQ ID NO: 165 | 3' GGACUGGGUGGGUUCUUGA 5' |
| SEQ ID NO: 70 | 5' GAACUUGCAGCUGAAGCCA 3' |
| | \|\|\|\|\|\|\|\|\|\|\|\|\|\|\|\|\|\|\| |
| SEQ ID NO: 166 | 3' CUUGAACGUCGACUUCGGU 5' |
| SEQ ID NO: 71 | 5' CUUGCAGCUGAAGCCAUUA 3' |
| | \|\|\|\|\|\|\|\|\|\|\|\|\|\|\|\|\|\|\| |
| SEQ ID NO: 167 | 3' GAACGUCGACUUCGGUAAU 5' |
| SEQ ID NO: 72 | 5' GCCAUUAAAGAAUUCUCGG 3' |
| | \|\|\|\|\|\|\|\|\|\|\|\|\|\|\|\|\|\|\| |
| SEQ ID NO: 168 | 3' CGGUAAUUUCUUAAGAGCC 5' |
| SEQ ID NO: 73 | 5' AGAAUUCUCGGCAGGUGGA 3' |
| | \|\|\|\|\|\|\|\|\|\|\|\|\|\|\|\|\|\|\| |
| SEQ ID NO: 169 | 3' UCUUAAGAGCCGUCCACCU 5' |
| SEQ ID NO: 74 | 5' GAAUUCUCGGCAGGUGGAG 3' |
| | \|\|\|\|\|\|\|\|\|\|\|\|\|\|\|\|\|\|\| |
| SEQ ID NO: 170 | 3' CUUAAGAGCCGUCCACCUC 5' |
| SEQ ID NO: 75 | 5' UUCUCGGCAGGUGGAGGUC 3' |
| | \|\|\|\|\|\|\|\|\|\|\|\|\|\|\|\|\|\|\| |
| SEQ ID NO: 171 | 3' AAGAGCCGUCCACCUCCAG 5' |
| SEQ ID NO: 76 | 5' AGAAAGAUAGAGUCUUCAC 3' |
| | \|\|\|\|\|\|\|\|\|\|\|\|\|\|\|\|\|\|\| |
| SEQ ID NO: 172 | 3' UCUUUCUAUCUCAGAAGUG 5' |
| SEQ ID NO: 77 | 5' GAAAGAUAGAGUCUUCACG 3' |
| | \|\|\|\|\|\|\|\|\|\|\|\|\|\|\|\|\|\|\| |
| SEQ ID NO: 173 | 3' CUUUCUAUCUCAGAAGUGC 5' |
| SEQ ID NO: 78 | 5' AGAUAGAGUCUUCACGGAC 3' |
| | \|\|\|\|\|\|\|\|\|\|\|\|\|\|\|\|\|\|\| |
| SEQ ID NO: 174 | 3' UCUAUCUCAGAAGUGCCUG 5' |
| SEQ ID NO: 79 | 5' GAUAGAGUCUUCACGGACA 3' |
| | \|\|\|\|\|\|\|\|\|\|\|\|\|\|\|\|\|\|\| |
| SEQ ID NO: 175 | 3' CUAUCUCAGAAGUGCCUGU 5' |
| SEQ ID NO: 80 | 5' GACCUCAGCCACGGUCAUC 3' |
| | \|\|\|\|\|\|\|\|\|\|\|\|\|\|\|\|\|\|\| |
| SEQ ID NO: 176 | 3' CUGGAGUCGGUGCCAGUAG 5' |
| SEQ ID NO: 81 | 5' AAAUGCCAGCAUUAGCGUG 3' |
| | \|\|\|\|\|\|\|\|\|\|\|\|\|\|\|\|\|\|\| |
| SEQ ID NO: 177 | 3' UUUACGGUCGUAAUCGCAC 5' |
| SEQ ID NO: 82 | 5' AAUGCCAGCAUUAGCGUGC 3' |
| | \|\|\|\|\|\|\|\|\|\|\|\|\|\|\|\|\|\|\| |
| SEQ ID NO: 178 | 3' UUACGGUCGUAAUCGCACG 5' |
| SEQ ID NO: 83 | 5' AUGCCAGCAUUAGCGUGCG 3' |
| | \|\|\|\|\|\|\|\|\|\|\|\|\|\|\|\|\|\|\| |
| SEQ ID NO: 179 | 3' UACGGUCGUAAUCGCACGC 5' |
| SEQ ID NO: 84 | 5' UGCCAGCAUUAGCGUGCGG 3' |
| | \|\|\|\|\|\|\|\|\|\|\|\|\|\|\|\|\|\|\| |
| SEQ ID NO: 180 | 3' ACGGUCGUAAUCGCACGCC 5' |
| SEQ ID NO: 85 | 5' UGGGCAUCUGUGCCCUGCA 3' |
| | \|\|\|\|\|\|\|\|\|\|\|\|\|\|\|\|\|\|\| |
| SEQ ID NO: 181 | 3' ACCCGUAGACACGGGACGU 5' |

Fig. 3
A
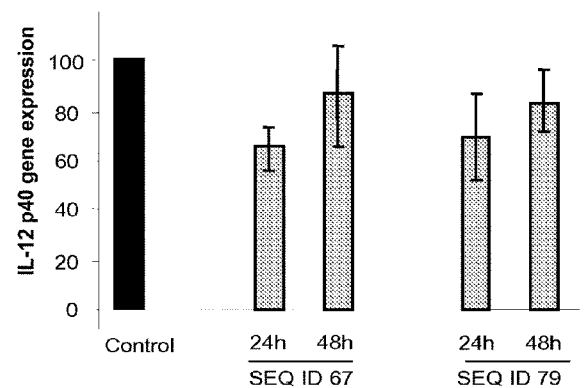
B
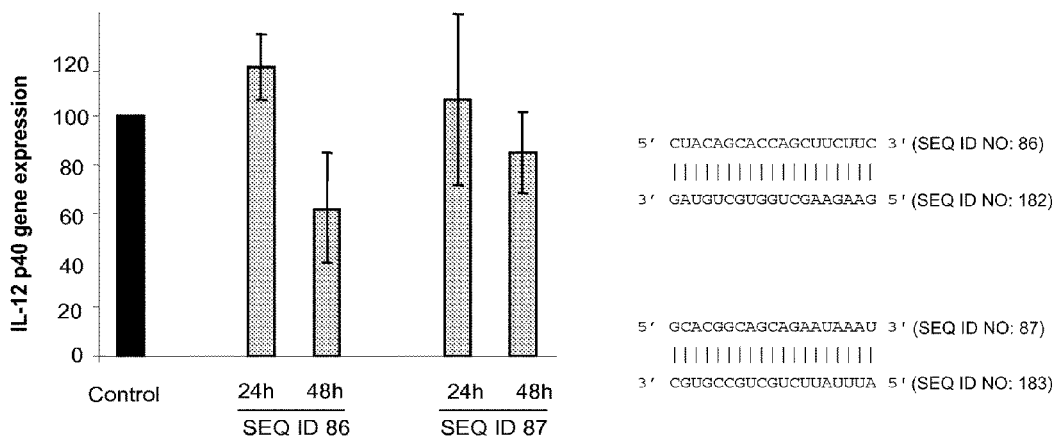

Fig. 8

| Small Intestine | % GFP expression | SEM | Large Intestine | % GFP expression | SEM |
|---|---|---|---|---|---|
| Control | 100 | 1,54 | Control | 100 | 0,47 |
|  |  |  |  |  |  |
| Mice 2-3 | 70 | 0,7 | Mice 2-3 | 68 | 0,26 |
|  |  |  |  |  |  |
| Mice 4-5 | 69 | 0,59 | Mice 4-5 | 75 | 0,33 |

Fig. 9:

| Small Intestine | % GFP expression | SEM | Large intestine | % GFP expression | SEM |
|---|---|---|---|---|---|
|  |  |  |  |  |  |
| Control | 100 | 0 | Control | 100 | 0 |
|  |  |  |  |  |  |
| Mice 2-3 | 38 | 0 | Mice 2-3 | 58 | 3,7 |
|  |  |  |  |  |  |
| Mice 4-5 | 27 | 6,3 | Mice 4-5 | 36 | 4,9 |

Fig. 16
A
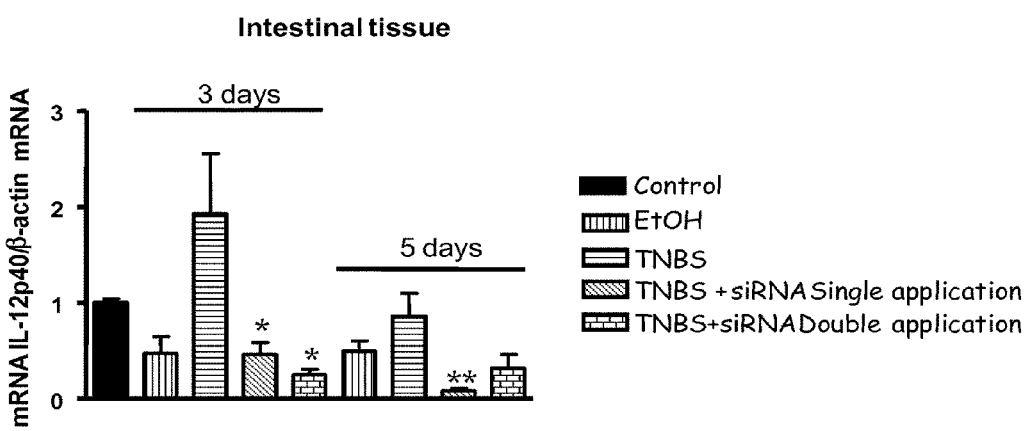
B
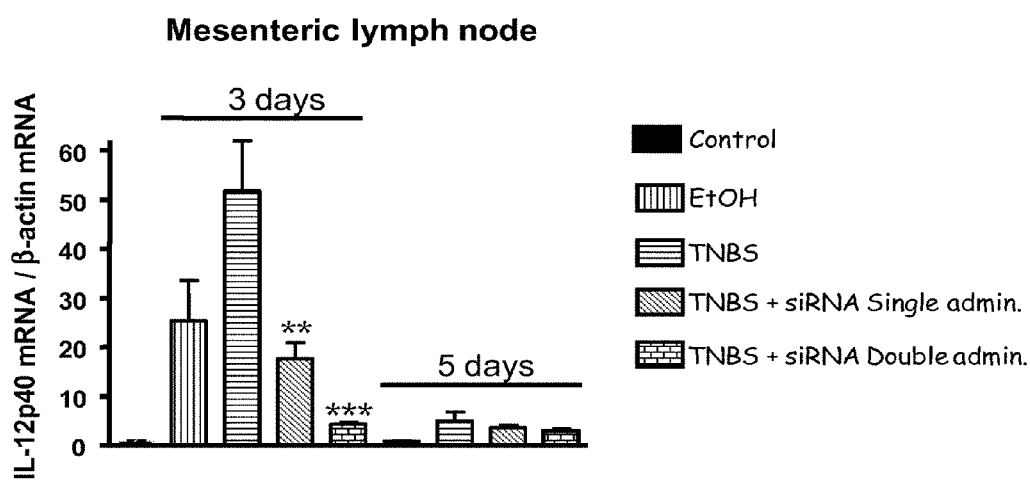

SEQUENCE LISTING

<160> NUMBER OF SEQ ID NOS: 183

<210> SEQ ID NO 1
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
uguucccaug ccuucacca                                              19

<210> SEQ ID NO 2
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
aaccugcuga gggccguca                                              19

<210> SEQ ID NO 3
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
caugcuccag aaggccaga                                              19

<210> SEQ ID NO 4
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
ggccagacaa acucuagaa                                              19

<210> SEQ ID NO 5
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
aaccagcaca guggaggcc                                              19

<210> SEQ ID NO 6
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6

-continued accagcacag uggaggccu                    19

<210> SEQ ID NO 7
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
ccaagaauga gaguugccu                    19

<210> SEQ ID NO 8
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
gaaugagagu ugccuaaau                    19

<210> SEQ ID NO 9
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
ugagaguugc cuaaauucc                    19

<210> SEQ ID NO 10
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
auuccagaga gaccucuuu                    19

<210> SEQ ID NO 11
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
uuccagagag accucuuuc                    19

<210> SEQ ID NO 12
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
cuaaugggag uugccuggc                    19

```
<210> SEQ ID NO 13
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
gacuugaaga uguaccagg                                                        19

<210> SEQ ID NO 14
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
gauguaccag guggaguuc                                                        19

<210> SEQ ID NO 15
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
gaccaugaau gcaaagcuu                                                        19

<210> SEQ ID NO 16
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
ugcaaagcuu cugauggau                                                        19

<210> SEQ ID NO 17
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
agcuucugau ggauccuaa                                                        19

<210> SEQ ID NO 18
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
gcuucugaug gauccuaag                                                        19

<210> SEQ ID NO 19
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
gaggcagauc uuucuagau                                                19

<210> SEQ ID NO 20
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
aacaugcugg caguuauug                                                19

<210> SEQ ID NO 21
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
acaugcuggc aguuauuga                                                19

<210> SEQ ID NO 22
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
caugcuggca guuauugau                                                19

<210> SEQ ID NO 23
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
uuucaacagu gagacugug                                                19

<210> SEQ ID NO 24
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
cagugagacu gugccacaa                                                19

<210> SEQ ID NO 25
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 25
aaauccuccc uugaagaac                                                    19

<210> SEQ ID NO 26
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
aauccucccu ugaagaacc                                                    19

<210> SEQ ID NO 27
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
auccucccuu gaagaaccg                                                    19

<210> SEQ ID NO 28
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
uccucccuug aagaaccgg                                                    19

<210> SEQ ID NO 29
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
aaucaagcuc ugcauacuu                                                    19

<210> SEQ ID NO 30
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
aucaagcucu gcauacuuc                                                    19

<210> SEQ ID NO 31
<211> LENGTH: 19
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 31
ucaagcucug cauacuucu                                                        19

<210> SEQ ID NO 32
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
gcucugcaua cuucuucau                                                        19

<210> SEQ ID NO 33
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
uucgggcagu gacuauuga                                                        19

<210> SEQ ID NO 34
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
uuggauuggu auccggaug                                                        19

<210> SEQ ID NO 35
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35 auggugguccc ucaccugug                                                       19

<210> SEQ ID NO 36
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
uggugguccu caccuguga                                                        19

<210> SEQ ID NO 37
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 37
gaagauggua ucaccugga                                                19

<210> SEQ ID NO 38
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
gaugguauca ccuggaccu                                                19

<210> SEQ ID NO 39
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
aacccugacc auccaaguc                                                19

<210> SEQ ID NO 40
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
acccugacca uccaaguca                                                19

<210> SEQ ID NO 41
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
cccugaccau ccaagucaa                                                19

<210> SEQ ID NO 42
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
gucaaagagu uuggagaug                                                19

<210> SEQ ID NO 43
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
```
agaguuugga gaugcuggc                                                19

<210> SEQ ID NO 44
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
gaguuuggag augcuggcc                                                19

<210> SEQ ID NO 45
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
aggaggcgag guucuaagc                                                19

<210> SEQ ID NO 46
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
ggaggcgagg uucuaagcc                                                19

<210> SEQ ID NO 47
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
gccauucgcu ccugcugcu                                                19

<210> SEQ ID NO 48
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
aaaggaagau ggaauuugg                                                19

<210> SEQ ID NO 49
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
aaggaagaug gaauuuggu                                                19

<210> SEQ ID NO 50
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
aggaagaugg aauuugguc                                                19

<210> SEQ ID NO 51
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
ggaagaugga auuuggucc                                                19

<210> SEQ ID NO 52
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
gauggaauuu gguccacug                                                19

<210> SEQ ID NO 53
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
aggaccagaa agaacccaa                                                19

<210> SEQ ID NO 54
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
ggaccagaaa gaacccaaa                                                19

<210> SEQ ID NO 55
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
uaagaccuuu cuaagaugc                                                19

```
<210> SEQ ID NO 56
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
gaccuuucua agaugcgag                                                    19

<210> SEQ ID NO 57
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
gaugcgaggc caagaauua                                                    19

<210> SEQ ID NO 58
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
gaauuauucu ggacguuuc                                                    19

<210> SEQ ID NO 59
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
uuauucugga cguucacc                                                     19

<210> SEQ ID NO 60
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
aagcagcaga ggcucuucu                                                    19

<210> SEQ ID NO 61
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
agcagcagag gcucuucug                                                    19

<210> SEQ ID NO 62
<211> LENGTH: 19
```

-continued

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
gcagcagagg cucuucuga                                                       19

<210> SEQ ID NO 63
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
caaggaguau gaguacuca                                                       19

<210> SEQ ID NO 64
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
ggaguaugag uacucagug                                                       19

<210> SEQ ID NO 65
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
aacuacacca gcagcuucu                                                       19

<210> SEQ ID NO 66
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
acuacaccag cagcuucuu                                                       19

<210> SEQ ID NO 67
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
cuacaccagc agcuucuuc                                                       19

<210> SEQ ID NO 68
<211> LENGTH: 19
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 68
accugaccca cccaagaac                                                      19

<210> SEQ ID NO 69
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
ccugacccac ccaagaacu                                                      19

<210> SEQ ID NO 70
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
gaacuugcag cugaagcca                                                      19

<210> SEQ ID NO 71
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
cuugcagcug aagccauua                                                      19

<210> SEQ ID NO 72
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
gccauuaaag aauucucgg                                                      19

<210> SEQ ID NO 73
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
agaauucucg gcaggugga                                                      19

<210> SEQ ID NO 74
<211> LENGTH: 19
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 74
gaauucucgg cagguggag                                                19

<210> SEQ ID NO 75
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
uucucggcag guggagguc                                                19

<210> SEQ ID NO 76
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
agaaagauag agucuucac                                                19

<210> SEQ ID NO 77
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
gaaagauaga gucuucacg                                                19

<210> SEQ ID NO 78
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
agauagaguc uucacggac                                                19

<210> SEQ ID NO 79
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
gauagagucu ucacggaca                                                19

<210> SEQ ID NO 80
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide -continued

<400> SEQUENCE: 80
gaccucagcc acggucauc                                                19

<210> SEQ ID NO 81
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
aaaugccagc auuagcgug                                                19

<210> SEQ ID NO 82
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
aaugccagca uuagcgugc                                                19

<210> SEQ ID NO 83
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
augccagcau uagcgugcg                                                19

<210> SEQ ID NO 84
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 84
ugccagcauu agcgugcgg                                                19

<210> SEQ ID NO 85
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85
ugggcaucug ugcccugca                                                19

<210> SEQ ID NO 86
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 86
cuacagcacc agcuucuuc                                                19

<210> SEQ ID NO 87
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87
gcacggcagc agaauaaau                                                19

<210> SEQ ID NO 88
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
ggcuacgucc aggagcgcac c                                             21

<210> SEQ ID NO 89
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89
ggcuacgucc aggagcgcac c                                             21

<210> SEQ ID NO 90
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 90
ugcgcuccug gacguagccu u                                             21

<210> SEQ ID NO 91
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 91
cuacagcacc agcuucuuc                                                19

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
agagggaaat cgtgcgtgac                                               20

```
<210> SEQ ID NO 93
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
caatagtgat gacctggccg t                                            21

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
ggaagcacgg cagcagaata                                              20

<210> SEQ ID NO 95
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
aacttgaggg agaagtagga atgg                                         24

<210> SEQ ID NO 96
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 96
gaagaagcug gugcuguag                                               19

<210> SEQ ID NO 97
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 97
uggugaaggc augggaaca                                               19

<210> SEQ ID NO 98
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 98
ugacggcccu cagcagguu                                               19

<210> SEQ ID NO 99
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 99
ucuggccuuc uggagcaug                                                    19

<210> SEQ ID NO 100
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 100
uucuagaguu ugucuggcc                                                    19

<210> SEQ ID NO 101
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 101
ggccuccacu gugcugguu                                                    19

<210> SEQ ID NO 102
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 102
aggccuccac ugugcuggu                                                    19

<210> SEQ ID NO 103
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 103
aggcaacucu cauucuugg                                                    19

<210> SEQ ID NO 104
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 104
auuuaggcaa cucucauuc                                                    19

<210> SEQ ID NO 105
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 105
ggaauuuagg caacucuca                                                  19

<210> SEQ ID NO 106
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 106
aaagaggucu cucuggaau                                                  19

<210> SEQ ID NO 107
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 107
gaaagagguc ucucuggaa                                                  19

<210> SEQ ID NO 108
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 108
gccaggcaac ucccauuag                                                  19

<210> SEQ ID NO 109
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 109
ccugguacau cuucaaguc                                                  19

<210> SEQ ID NO 110
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 110
gaacuccacc ugguacauc                                                  19

<210> SEQ ID NO 111
<211> LENGTH: 19
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 111
aagcuuugca uucaugguc                                                      19

<210> SEQ ID NO 112
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 112
auccaucaga agcuuugca                                                      19

<210> SEQ ID NO 113
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 113
uuaggaucca ucagaagcu                                                      19

<210> SEQ ID NO 114
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 114
cuuaggaucc aucagaagc                                                      19

<210> SEQ ID NO 115
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 115
aucuagaaag aucugccuc                                                      19

<210> SEQ ID NO 116
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 116
caauaacugc cagcauguu                                                      19

<210> SEQ ID NO 117
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 117
ucaauaacug ccagcaugu                                                19

<210> SEQ ID NO 118
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 118
aucaauaacu gccagcaug                                                19

<210> SEQ ID NO 119
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 119
cacagucuca cuguugaaa                                                19

<210> SEQ ID NO 120
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 120
uuguggcaca gucucacug                                                19

<210> SEQ ID NO 121
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 121
guucuucaag ggaggauuu                                                19

<210> SEQ ID NO 122
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 122
gguucuucaa gggaggauu                                                19

<210> SEQ ID NO 123
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 123
cgguucuuca agggaggau                                              19

<210> SEQ ID NO 124
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 124
ccgguucuuc aagggagga                                              19

<210> SEQ ID NO 125
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 125
aaguaugcag agcuugauu                                              19

<210> SEQ ID NO 126
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 126
gaaguaugca gagcuugau                                              19

<210> SEQ ID NO 127
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 127
agaaguaugc agagcuuga                                              19

<210> SEQ ID NO 128
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 128
augaagaagu augcagagc                                              19

<210> SEQ ID NO 129
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 129
ucaauaguca cugcccgaa                                              19

```
<210> SEQ ID NO 130
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 130
cauccggaua ccaauccaa                                                     19

<210> SEQ ID NO 131
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 131
cacaggugag gaccaccau                                                     19

<210> SEQ ID NO 132
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 132
ucacagguga ggaccacca                                                     19

<210> SEQ ID NO 133
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 133
uccaggugau accaucuuc                                                     19

<210> SEQ ID NO 134
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 134
agguccaggu gauaccauc                                                     19

<210> SEQ ID NO 135
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 135
gacuuggaug gucagggüu                                                     19
```

```
<210> SEQ ID NO 136
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 136
ugacuuggau ggucagggu                                            19

<210> SEQ ID NO 137
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 137
uugacuugga uggucaggg                                            19

<210> SEQ ID NO 138
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 138
caucuccaaa cucuuugac                                            19

<210> SEQ ID NO 139
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 139
gccagcaucu ccaaacucu                                            19

<210> SEQ ID NO 140
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 140
ggccagcauc uccaaacuc                                            19

<210> SEQ ID NO 141
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 141
gcuuagaacc ucgccuccu                                            19

<210> SEQ ID NO 142
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 142
ggcuuagaac cucgccucc                                                   19

<210> SEQ ID NO 143
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 143
agcagcagga gcgaauggc                                                   19

<210> SEQ ID NO 144
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 144
ccaaauucca ucuuccuuu                                                   19

<210> SEQ ID NO 145
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 145
accaaauucc aucuuccuu                                                   19

<210> SEQ ID NO 146
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 146
gaccaaauuc caucuuccu                                                   19

<210> SEQ ID NO 147
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 147
ggaccaaauu ccaucuucc                                                   19

<210> SEQ ID NO 148
<211> LENGTH: 19
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 148
caguggacca aauuccauc                                                      19

<210> SEQ ID NO 149
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 149
uuggguucuu ucugguccu                                                      19

<210> SEQ ID NO 150
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 150
uuuggguucu ucuggucc                                                       19

<210> SEQ ID NO 151
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 151
gcaucuuaga aagucuua                                                       19

<210> SEQ ID NO 152
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 152
cucgcaucuu agaaagguc                                                      19

<210> SEQ ID NO 153
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 153
uaauucuugg ccucgcauc                                                      19

<210> SEQ ID NO 154
<211> LENGTH: 19
<212> TYPE: RNA
<213> ORGANISM: Artificial Sequence
<220> FEATURE:
<223> OTHER INFORMATION: Description of Artificial Sequence: Synthetic
```

-continued

```
      oligonucleotide

<400> SEQUENCE: 154
gaaacgucca gaauaauuc                                                      19

<210> SEQ ID NO 155
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 155
ggugaaacgu ccagaauaa                                                      19

<210> SEQ ID NO 156
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 156
agaagagccu cugcugcuu                                                      19

<210> SEQ ID NO 157
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 157
cagaagagcc ucugcugcu                                                      19

<210> SEQ ID NO 158
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 158
ucagaagagc cucugcugc                                                      19

<210> SEQ ID NO 159
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 159
ugaguacuca uacuccuug                                                      19

<210> SEQ ID NO 160
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 160
cacugaguac ucauacucc                                                19

<210> SEQ ID NO 161
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 161
agaagcugcu gguguaguu                                                19

<210> SEQ ID NO 162
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 162
aagaagcugc ugguguagu                                                19

<210> SEQ ID NO 163
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 163
gaagaagcug cugguguag                                                19

<210> SEQ ID NO 164
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 164
guucuugggu gggucaggu                                                19

<210> SEQ ID NO 165
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 165
aguucuuggg ugggucagg                                                19

<210> SEQ ID NO 166
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 166
```
uggcuucagc ugcaaguuc                                              19

<210> SEQ ID NO 167
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 167
uaauggcuuc agcugcaag                                              19

<210> SEQ ID NO 168
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 168
ccgagaauuc uuuaauggc                                              19

<210> SEQ ID NO 169
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 169
uccaccugcc gagaauucu                                              19

<210> SEQ ID NO 170
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 170
cuccaccugc cgagaauuc                                              19

<210> SEQ ID NO 171
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 171
gaccuccacc ugccgagaa                                              19

<210> SEQ ID NO 172
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 172
gugaagacuc uaucuuucu                                              19

```
<210> SEQ ID NO 173
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 173
cgugaagacu cuaucuuuc                                                   19

<210> SEQ ID NO 174
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 174
guccgugaag acucuaucu                                                   19

<210> SEQ ID NO 175
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 175
uguccgugaa gacucuauc                                                   19

<210> SEQ ID NO 176
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 176
gaugaccgug gcugagguc                                                   19

<210> SEQ ID NO 177
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 177
cacgcuaaug cuggcauuu                                                   19

<210> SEQ ID NO 178
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 178
gcacgcuaau gcuggcauu                                              19

<210> SEQ ID NO 179
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 179
cgcacgcuaa ugcuggcau                                              19

<210> SEQ ID NO 180
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 180
ccgcacgcua augcuggca                                              19

<210> SEQ ID NO 181
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 181
ugcagggcac agaugccca                                              19

<210> SEQ ID NO 182
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 182
gaagaagcug gugcuguag                                              19

<210> SEQ ID NO 183
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 183
auuuauucug cugccgugc                                              19
```

METHODS AND COMPOSITIONS FOR THE TREATMENT OF INTESTINAL CONDITIONS

This application is a Divisional Application under 35 U.S.C §121 of U.S. application Ser. No. 11/858,579, filed Sep. 20, 2007 now U.S. Pat. No. 7,807,650, which is a continuation-in-part of International Patent Application No. PCT/GB2006/050051, filed Mar. 14, 2006, which claims priority to British Application GB0505081.0, filed Mar. 14, 2005, the contents of which are each herein incorporated by reference in its entirety.

FIELD OF THE INVENTION

The present invention relates to methods and compositions for the treatment of intestinal pathologies by means of intrarectal administration of Nucleic Acid interference (NAi) technology. The compositions of the invention comprise short interfering nucleic acid molecules (siNA) and related compounds including, but not limited to, small-interfering RNAs (siRNA). In particular, the compositions of the invention can be used for the treatment of intestinal pathologies including: hyperproliferative diseases, in particular, colorectal cancer; autoimmune and inflammatory bowel diseases (IBD), in particular Crohn's disease; colitis, in particular ulcerative colitis; irritable bowel syndrome; infectious diseases of the intestine, such as pseudomembranous colitis, amebiasis or intestinal tuberculosis; colonic polyps; diverticular disease; constipation; intestinal obstruction; malabsorption syndromes; rectal diseases and diarrhoea.

In more specific embodiments, the present invention refers to treatment of intestinal conditions caused by increased levels of interleukin-12 (IL-12), a cytokine involved in T helper type 1 (Th1) cell immune response. Such intestinal conditions include, for example, autoimmune diseases and IBD. Compositions and methods comprising siRNA and related compounds targeting IL12-p40 subunit and/or IL12-p35 subunit are provided for the treatment of diseases associated with over-expression of IL-12, in particular Crohn's disease.

BACKGROUND OF THE INVENTION

RNA interference refers to the process of sequence-specific post-transcriptional gene silencing mediated by double-stranded RNA (dsRNA). After the discovery of the phenomenon in plants in the early 1990s, specific and selective inhibition of gene expression in an extremely efficient manner in *Caenorhabditis elegans* using dsRNA was reported (Fire et al., 1998). The sequence of the first strand (sense RNA) coincided with that of the corresponding region of the target messenger RNA (mRNA). The second strand (antisense RNA) was complementary to the mRNA. The resulting dsRNA turned out to be several orders of magnitude more efficient than the corresponding single-stranded RNA molecules (in particular, antisense RNA).

The process of RNAi begins when the enzyme DICER encounters dsRNA and chops it into pieces called small-interfering RNAs or siRNAs. This protein belongs to the RNase III nuclease family. A complex of proteins gathers up these siRNAs and uses their code as a guide to search out and destroy any RNAs in the cell with a matching sequence, such as target mRNA (see Bosher & Labouesse, 2000, Nat Cell Biol, 2000, 2(2):E31; and Akashi et al., 2001, Antisense Nucleic Acid Drug Dev, 11(6):359).

In attempting to use RNAi for gene knockdown, it was recognized that mammalian cells have developed various protective mechanisms against viral infections that could impede the use of this approach. Indeed, the presence of extremely low levels of viral dsRNA triggers an interferon response, resulting in a global non-specific suppression of translation, which in turn triggers apoptosis (Williams, 1997, Biochem Soc Trans, 25(2):509; Gil & Esteban, 2000, Apoptosis, 5(2): 107-14).

In 2000, dsRNA was reported to specifically inhibit three genes in the mouse oocyte and early embryo. Translational arrest, and thus a PKR response, was not observed as the embryos continued to develop (Wianny & Zernicka-Goetz, 2000, Nat Cell Biol, 2(2):70). Research at Ribopharma AG (Kulmbach, Germany) reported the functionality of RNAi in mammalian cells, using short (20-24 base pairs) dsRNAs to switch off genes in human cells without initiating the acute-phase response. Similar experiments carried out by other research groups confirmed these results (Elbashir et al., 2001, Genes Dev, 15(2):188; Caplen et al., 2001, Proc. Natl. Acad. Sci. USA, 98:9742). Tested in a variety of normal and cancer human and mouse cell lines, it was determined that short hairpin RNAs (shRNAs) can silence genes as efficiently as their siRNA counterparts (Paddison et al., 2002, Genes Dev, 16(8):948). Recently, another group of small RNAs (21-25 base pairs) was shown to mediate downregulation of gene expression. These RNAs, small temporally regulated RNAs (stRNAs), regulate timing of gene expression during development in *Caenorhabditis elegans* (for review see Banerjee & Slack, 2002 and Grosshans & Slack, 2002, J Cell Biol, 156 (1):17).

Scientists have used RNAi in several systems, including *Caenorhabditis elegans, Drosophila*, trypanosomes, and other invertebrates. Several groups have recently presented the specific suppression of protein biosynthesis in different mammalian cell lines (specifically in HeLa cells) demonstrating that RNAi is a broadly applicable method for gene silencing in vitro. Based on these results, RNAi has rapidly become a well recognized tool for validating (identifying and assigning) gene functions. RNAi employing short dsRNA oligonucleotides will yield an understanding of the function of genes being only partially sequenced.

Recently, Krutzfeldt and colleagues have shown that a class of specially engineered compounds called 'antagomirs' can effectively silence the action of microRNAs (miRNAs), non-coding pieces of RNA that regulate gene expression (Krutzfeldt et al., 2005, Nature, 438(7068):685-9).

The preceding is a discussion of relevant art pertaining to RNAi. The discussion is provided only for understanding of the invention that follows, and is not an admission that any of the work described is prior art to the claimed invention.

Although potential applications of siRNA technology are vast in medical science, their administration and delivery to the desired site of action proves a significant complication, due mainly to ubiquitous expression of RNAses. In fact, in the state of the art, delivery is achieved mainly, by direct injection into the desired tissue, this form of administration not being appropriate for treatment of many different diseases. For example, the treatment of intestinal conditions affecting the whole intestine or a significant portion, via the injection of formulations containing siRNAs into the intestinal tissue would be highly impractical, due to the dimensions of the organ.

This invention relates to a method for intestinal delivery of siRNA, and provides a specific example of the same comprising treatment of Crohn's disease via administration of IL-12 specific siRNA.

Interleukin-12 (IL-12) is a heterodimeric 70 kDa glycoprotein (IL12-p70) consisting of a 40 kDa subunit (designated IL12-p40) and a 35 kDa subunit (designated IL12-p35) linked by disulfide bonds that are essential for the biological activity of IL-12.

IL-12 is a key cytokine that regulates cell-mediated immune responses and type 1 T helper (Th1) cell inflammatory reactions (Gately et al., 1998 Annu Rev Immunol. 16:495-521; Trinchieri, 1998, Adv Immunol. 70:83-243).

One particular IBD is Crohn's disease, a pathology characterized by an increased production of IL-12 by antigen-presenting cells in intestinal tissue and interferon-γ and tumor necrosis factor α (TNF-α) by intestinal lymphocytes and macrophages (Fais et al., 1994, J Interferon Res. 14(5):235-8; Fuss et al., 1996, J Immunol. 157(3):1261-70; Monteleone et al., 1997 Gastroenterology, 112(4):1169-78; Parronchi et al., 1997 Am J Pathol. 150(3):823-32; Plevy et al., 1997, J Immunol. 15; 159(12):6276-82).

Crohn's disease causes inflammation in the small intestine. The inflammation can cause pain and can make the intestines empty frequently, resulting in diarrhoea. The most common symptoms of Crohn's disease are abdominal pain and diarrhoea, although rectal bleeding, weight loss and fever may also occur. Bleeding may be serious and persistent, leading to anaemia. Children with Crohn's disease may suffer delayed development and stunted growth.

Most people are first treated with drugs containing mesalamine, a substance that helps control inflammation. Sulfasalazine is the most commonly used of these drugs. Patients who do not benefit from it or who cannot tolerate it may be put on other mesalamine-containing drugs, generally known as 5-ASA agents, such as Asacol, Dipentum or Pentasa. Possible side-effects of mesalamine preparations include nausea, vomiting, diarrhoea and headache. Some patients take corticosteroids to control inflammation. These drugs are the most effective for active Crohn's disease, but they can cause serious side effects, including greater susceptibility to infection. Drugs that suppress the immune system are also used to treat Crohn's disease. Most commonly prescribed are 6-mercaptopurine and a related drug, azathioprine. Immunosuppressive agents work by blocking the immune reaction that contributes to inflammation. These drugs may cause side effects like nausea, vomiting, and diarrhoea and may lower a person's resistance to infection. Surgery to remove part of the intestine can help Crohn's disease but cannot cure it. Due to the side effects and the lack of effectiveness of the current treatments for Crohn's disease, researchers continue to look for more effective treatments.

Inhibiting the action of IL-12 has been shown to suppress development and clinical progression of disease in a multitude of experimental models of autoimmunity and chronic inflammation (Caspi, 1998, Clin Immunol Immunopathol. 88(1):4-13). These models include experimental autoimmune encephalomyelitis (EAE), experimental autoimmune uveitis (EAU), collagen-induced arthritis (CIA), autoimmune nephritis, insulin-dependent diabetes mellitus (IDDM) and different models for IBD (Vandenbroeck et al., 2004, J Pharm Pharmacol. 56(2):145-60). In these models, the role of endogenous IL-12 has been addressed by using IL-12p40 knockout mice or by administering anti-IL-12 antibodies.

In particular, targeting IL-12 with antibodies is an effective treatment for the intestinal inflammation in animal models of Crohn's disease (Mannon et al., 2004, N Engl J Med. 351 (20):2069-79). Thus, mice with trinitrobenzene sulfonate-induced colitis have a Th1-mediated gut inflammation characterized by greatly increased production of IL-12, interferon-γ and tumour necrosis factor α (TNF-α). In mice, administration of a monoclonal antibody against IL-12 can result in the resolution of established colitis and, if given at the time of induction of colitis, can prevent inflammation (Neurath et al., 1995, J Exp Med. 182(5):1281-90).

Anti-interleukin-12 can also prevent and treat the spontaneous colitis seen in models of Th1-mediated inflammation such as mice that over-express the human CD3ε gene and mice deficient in interleukin-10 (Davidson et al., 1998; Simpson et al., 1998).

Data from an early phase 2 study provide some evidence that treatment with a monoclonal antibody against IL-12 p40 may induce clinical response and remission in patients with active Crohn's disease (Mannon et al., 2004). This treatment is associated with decreases in Th1-mediated inflammatory cytokines at the site of disease.

Previous evidence obtained from animal models, as well as the clinical effects of anti-IL-12 in patients with Crohn's disease (Mannon et al., 2004, N Engl J Med. 351(20):2069-79), highlight the importance of IL-12 as a target for future treatments for Crohn's disease.

siRNA targeting of IL-12 expression has already been used to obtain modified dendritic cells (DC) that might be used in a variety of therapeutic in vitro, ex vivo and in vivo methods to modulate T cell activity, and thus have use in therapeutic approaches for the treatment of immune disorders in a mammalian subject (WO 03/104456; Hill et al., 2003, J Immunol. 171(2):691-6). siRNA targeting of IL-12 expression in mature DC has revealed a critical role for IL-12 in natural killer cell interferon γ (IFN-γ) secretion promoted by mature DC (Borg et al., 2004, Blood 104(10):3267-75). Further, IL-12 p35 inhibitors including siRNA have surprisingly demonstrated to block differentiation of preadipocytes to adipocytes and triglyceride accumulation in adipocytes (WO 03/104495).

siRNA targeting IL-12p40 delivered by means of liposome encapsulation to murine peritoneal cavity has been reported to modulate the local and systemic inflammatory response after endotoxin challenge (Flynn et al., 2004, J Inflamm 1(1): 4).

SUMMARY OF THE INVENTION

This invention relates to methods and compositions for the treatment of intestinal disorders by administration of short interfering nucleic acid (siNA) molecules to the intestine. The compositions of the invention comprise short interfering nucleic acid molecules (siNA) and related compounds including, but not limited to, siRNA. In particular, the compositions of the invention can be used in the preparation of a medicament for the treatment of intestinal pathologies including: hyperproliferative diseases, such as colorectal cancer; autoimmune and inflammatory bowel diseases (IBD), such as Crohn's disease; colitis, in particular ulcerative colitis; irritable bowel syndrome; infectious diseases of the intestine, such as pseudomembranous colitis, amebiasis or intestinal tuberculosis; colonic polyps; diverticular disease; constipation; intestinal obstruction; malabsorption syndromes; rectal diseases and diarrhoea. This invention encompasses compositions and methods of use of siNA including, but not limited to, short interfering RNA (siRNA), double-stranded RNA (dsRNA), micro-RNA (miRNA), antagomirs and short hairpin RNA (shRNA) molecules capable of mediating RNA interference against genes involved in the above mentioned pathologies, preferably genes which are upregulated in such conditions. siNAs of the invention can be unmodified or chemically modified.

The methods of the invention comprise the administration to a patient in the need thereof of an effective amount of one or more siNA of the invention for the treatment of an intestinal condition. Administration of one or more siNA is accomplished so as to deliver siNA to the intestine, preferably to the region of the intestine involved in the disease or condition to be treated. In preferred embodiments, the methods of the invention comprise intrarectal administration of the therapeutic siNA.

In a specific embodiment, the present invention relates to siNA or similar chemically synthesized entities that are directed at interfering with the mRNA expression of either p35 or p40 subunits of the cytokine IL-12, that ultimately modulate the amount of protein produced. Compositions and methods comprising the above-mentioned siRNAs and related compounds are intended for the treatment of intestinal diseases associated with over-expression of IL-12, such as autoimmune diseases and inflammatory bowel diseases (IBD), in particular, Crohn's disease, and those listed above.

BRIEF DESCRIPTION OF THE DRAWINGS

FIG. 1: Oligonucleotide sequences for siRNA molecules targeting IL-12 p35 and p40 subunits encompassed by the present invention. The SEQ ID Nos. given in the Figure refer to the sense (5'->3') strand; typically siRNA will be administered as dsRNA, so will include both the sense strand and its complement. SEQ ID NOS 1-85 are disclosed respectively in order of appearance.

FIGS. 3A-3B: Effect of siRNA on IL-12 p40 subunit expression in an in vitro system. (A) siRNA treatment reduces the levels of IL-12 p40 gene transcript in human cells. RNA was prepared from SW480 cells treated with siRNA SEQ ID NO: 67 and SEQ ID NO: 79 at different times, at dose treatment of 200 nM. The values show the mean expression levels of different transcripts normalized to 18S as housekeeping gene. The values represent the mean of the percentage of the normalized mRNA levels upon siRNA interference over the control gene expression and their medium standard deviations (SEM). (B) siRNA treatment reduces the levels of IL-12 p40 gene transcript in murine cells. RNA was prepared from C2C12 cells treated with siRNA SEQ ID NO: 86 and SEQ ID NO: 87 at different times, at dose treatment of 100 nM. SEQ ID NO: 86, which is homologous to human SEQ ID NO: 67, targets the mouse IL-12 p40 subunit. Further targeting the mouse IL-12 p40 subunit, SEQ ID NO: 87 is the siRNA with the best score in mouse, and has no homologous siRNA duplex in human. siNA molecules SEQ ID NO: 86 and SEQ ID NO: 87 are as described below, with 2 thymidine nucleotide 3' overhangs. The values represent the mean of the percentage of the normalized mRNA levels compared to 18S upon siRNA interference over the control gene expression and their medium standard deviations (SEM).

FIG. 8: Data of samples collected in OCT medium.

FIG. 9: Data of samples collected in RNA LATER®

FIGS. 16A-16B: Analysis of IL-12p40 mRNA expression levels in intestinal tissue (A) or mesenteric lymph nodes (B) from mice belonging to previously described treatment groups. The ratio of IL-12p40 vs. β-actin mRNA expression levels was determined in control mice that received one dose of NaCl, and mice treated according to conditions described previously. Relative values for each treatment were calculated and represented in relation to control levels.

DETAILED DESCRIPTION OF THE INVENTION

Figure 2:
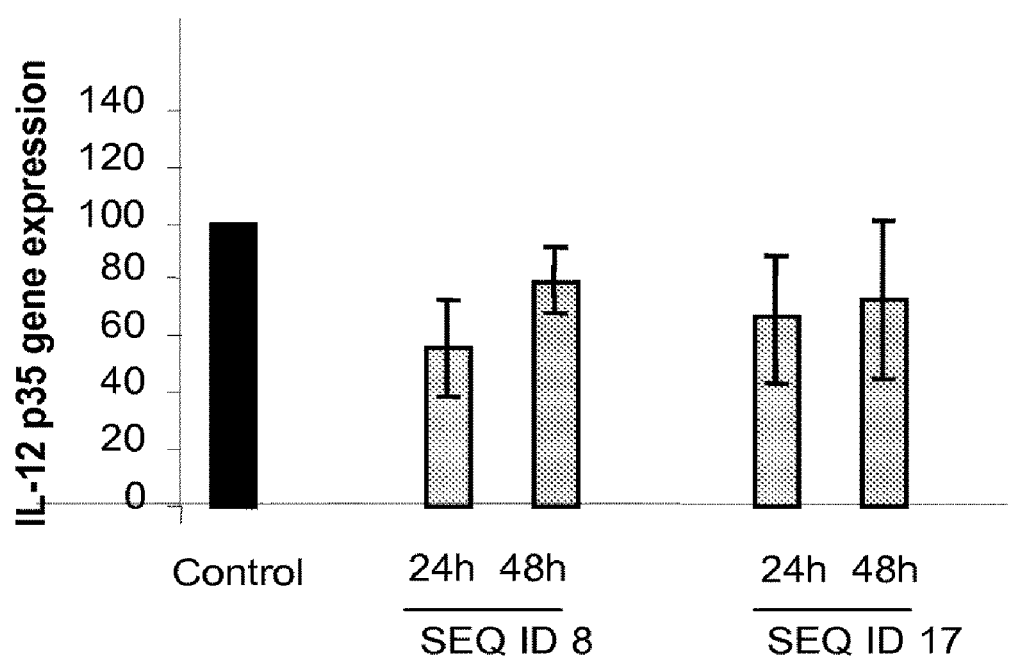
FIG. 2: Effect of siRNA on IL-12 p35 subunit expression in an in vitro system. siRNA treatment reduces the levels of IL-12 p35 gene transcript. RNA was prepared from SW480 cells treated with siRNAs for different times. The samples were analyzed by RT-PCR using specific primers. The values show the mean expression levels of different transcripts normalized to 18S as housekeeping gene.

This invention relates to methods and compositions for the treatment of intestinal pathologies by means of intestinal administration of the short interfering Nucleic Acid (siNA) molecules. The compositions of the invention comprise short interfering nucleic acid molecules (siNA) that modulate the expression of target genes associated with conditions of the intestinal wall.

The methods of the invention comprise the administration to a patient in need thereof of an effective amount of one or more siNA of the invention. The compositions of the invention can be used in the preparation of a medicament for the treatment of intestinal conditions including hyperproliferative diseases, such as colorectal cancer; autoimmune and inflammatory bowel diseases (IBD), such as Crohn's disease; colitis, in particular ulcerative colitis; irritable bowel syndrome; infectious diseases of the intestine, such as pseudomembranous colitis, amebiasis or intestinal tuberculosis; colonic polyps; diverticular disease; constipation; intestinal obstruction; malabsorption syndromes; rectal diseases and diarrhoea.

Design of siNA

A gene is "targeted" by siNA according to the invention when, for example, the siNA molecule selectively decreases or inhibits the expression of the gene. The term "selectively decrease or inhibit" as used herein encompasses siNAs that affect expression of one gene as well as those that affect the expression of more than one gene. In cases where an siNA affects expression of more than one gene, the gene that is targeted is effected at least two times, three times, four times, five times, ten times, twenty time, fifty times, or one hundred times as much as any other gene. Alternatively, a siNA targets a gene when the siNA hybridizes under stringent conditions to the gene transcript. siNA can be tested either in vitro or in vivo for the ability to target a gene.

In 1999, Tuschl et al. (Genes Dev. 1999, 13(24):3191-7) deciphered the silencing effect of siRNAs showing that their efficiency is a function of the length of the duplex, the length of the 3'-end overhangs, and the sequence in these overhangs.

Selecting the right homologous region within the target gene is of great relevance for accurate silencing. A short fragment of the target gene sequence (e.g., 19-40 nucleotides in length) is chosen as the sequence of the siNA of the invention. In one embodiment, the siNA is siRNA. In such embodiments, the short fragment of target gene sequence is a fragment of the target gene mRNA. In preferred embodiments, the criteria for choosing a sequence fragment from the target gene mRNA to be a candidate siRNA molecule include: 1) a sequence from the target gene mRNA that is at least 50-100 nucleotides from the 5' or 3' end of the native mRNA molecule; 2) a sequence from the target gene mRNA that has a G/C content of between 30% and 70%, most preferably around 50%; 3) a sequence from the target gene mRNA that does not contain repetitive sequences (e.g., AAA, CCC, GGG, TTT, AAAA, CCCC, GGGG, TTTT); 4) a sequence from the target gene mRNA that is accessible in the mRNA; and 5) a sequence from the target gene mRNA that is unique to the target gene. The sequence fragment from the target gene mRNA may meet one or more of the above-mentioned identified criteria. In embodiments where a fragment of the target gene mRNA meets less than all of the criteria identified above, the native sequence may be altered such that the siRNA conforms with more of the criteria than does the fragment of the target gene mRNA. In preferred embodiments, the siRNA has a G/C content below 60% and/or lacks repetitive sequences.

Practically, the gene of interest is introduced as a nucleotide sequence in a prediction program that takes into account all the variables described above for the design of optimal oligonucleotides. This program scans any mRNA nucleotide sequence for regions susceptible to be targeted by siRNA. The output of this analysis is a score of possible siRNA oligonucleotides. The highest scores are used to design double stranded RNA oligonucleotides (typically 21 bp long, although other lengths are also possible) that are typically made by chemical synthesis. The present invention also comprises siNAs containing one or more of several chemical modifications that are well known in the art. These modifications are aimed at increasing stability or availability of the dsRNA oligonucleotides.

Candidate oligonucleotides can further be filtered for interspecies sequence conservation in order to facilitate the transition from animal to human clinical studies.

In some embodiments, each of the siNAs of the invention targets one gene. In one specific embodiment, the portion of the siNA that is complementary to the target region is perfectly complementary to the target region. In another specific embodiment, the portion of the siNA that is complementary to the target region is not perfectly complementary to the target region. siNA with insertions, deletions and point mutations relative to the target sequence are also encompassed by the invention.

In addition to siNA which is perfectly complementary to the target region, degenerate siNA sequences may be used to target homologous regions of multiple genes. WO2005/045037 describes the design of siNA molecules to target such homologous sequences, for example by incorporating non-canonical base pairs, for example mismatches and/or wobble base pairs, that can provide additional target sequences. In instances where mismatches are identified, non-canonical base pairs (for example, mismatches and/or wobble bases) can be used to generate siNA molecules that target more than one gene sequence. In a non-limiting example, non-canonical base pairs such as UU and CC base pairs are used to generate siNA molecules that are capable of targeting sequences for differing targets that share sequence homology. As such, one advantage of using siNAs of the invention is that a single siNA can be designed to include nucleic acid sequence that is complementary to the nucleotide sequence that is conserved between homologous genes. In this approach, a single siNA can be used to inhibit expression of more than one gene instead of using more than one siNA molecule to target different genes.

Sequence identity may be calculated by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90%, 95%, or 99% sequence identity between the siNA and the portion of the target gene is preferred. Alternatively, the complementarity between the siNA and native RNA molecule may be defined functionally by hybridization (e.g. 400 mM NaCl, 40 mM PIPES pH 6.4, 1 mM EDTA, 50° C. or 70° C., hybridization for 12-16 hours; followed by washing). A siNA sequence of the invention can also be defined functionally by its ability to decrease or inhibit the expression of a target gene. The ability of a siNA to affect gene expression can be determined empirically either in vivo or in vitro.

Preferred siNA molecules of the invention are double stranded. In one embodiment, double stranded siNA molecules comprise blunt ends. In another embodiment, double stranded siNA molecules comprise overhanging nucleotides (e.g., 1-5 nucleotide overhangs, preferably 2 nucleotide overhangs). In a specific embodiment, the overhanging nucleotides are 3' overhangs. In another specific embodiment, the overhanging nucleotides are 5' overhangs. Any type of nucleotide can be a part of the overhang. In one embodiment, the overhanging nucleotide or nucleotides are ribonucleic acids. In another embodiment, the overhanging nucleotide or nucleotides are deoxyribonucleic acids. In a preferred embodiment, the overhanging nucleotide or nucleotides are thymidine nucleotides. In another embodiment, the overhanging nucleotide or nucleotides are modified or non-classical nucleotides. The overhanging nucleotide or nucleotides may have non-classical internucleotide bonds (e.g., other than phosphodiester bond).

On the other hand, the endogenous miRNA pathway serves as a cellular rheostat for fine-tuning gene expression during, especially during development and differentiation. The 3' untranslated regions of mRNAs are targeted by miRNAs with which they share partial sequence complementarity, which is often accompanied by subsequent mRNA degradation. When a miRNA has complete sequence complementarity with a target mRNA, it instead directs cleavage of the mRNA transcript through RISC activity. This is a naturally occurring gene expression regulating system in eukaryote cells. As indicated above, it is possible to target miRNA for degradation using specific siRNA. In this scenario it would be possible to obtain upregulation of the desired gene expression, or modulation (increasing or decreasing mRNA levels) of the expression of another gene further downstream in the regulation pathway. Therefore, siRNAs targeted to specific miRNAs involved in intestinal disorders are also an object of the present invention.

Synthesis of siNA Duplexes siNA can be synthesized by any method known in the art. RNAs are preferably chemically synthesized using appropriately protected ribonucleoside phosphoramidites and a conventional DNA/RNA synthesizer. Additionally, siRNA can be obtained from commercial RNA oligo synthesis suppliers, including, but not limited to, Proligo (Hamburg, Germany), Dharmacon Research (Lafayette, Colo., USA), Glen Research (Sterling, Va., USA), ChemGenes (Ashland, Mass., USA), and Cruachem (Glasgow, UK), Qiagen (Germany) Ambion (USA) and Invitrogen (Scotland). Alternatively, siNA molecules of the invention can be expressed in cells by transfecting the cells with vectors containing the reverse complement siNA sequence under the control of a promoter. Once expressed, the siNA can be isolated from the cell using techniques well known in the art.

In embodiments where the siRNA is a dsRNA, an annealing step is necessary if single-stranded RNA molecules are obtained. To anneal the RNAs, 30 μl of each RNA oligo 50 μM solution are to be combined in 100 mM potassium acetate, 30 mM HEPES-KOH pH 7.4, 2 mM magnesium acetate. The solution is then incubated for 1 minute at 90° C., centrifuged for 15 seconds, and incubated for 1 hour at 37° C.

In embodiments where the siRNA is a short hairpin RNA (shRNA); the two strands of the siRNA molecule may be connected by a linker region (e.g., a nucleotide linker or a non-nucleotide linker).

Chemical Modification of siNA.

The siNAs of the invention may contain one or more modified nucleotides and/or non-phosphodiester linkages. Chemical modifications well known in the art are capable of increasing stability, availability, and/or cell uptake of the siNA. The skilled person will be aware of other types of chemical modification which may be incorporated into RNA molecules (see International Publications WO03/070744 and WO2005/045037 for an overview of types of modifications).

In one embodiment, modifications can be used to provide improved resistance to degradation or improved uptake. Examples of such modifications include phosphorothioate internucleotide linkages, 2'-O-methyl ribonucleotides (especially on the sense strand of a double stranded siRNA), 2'-deoxy-fluoro ribonucleotides, 2'-deoxy ribonucleotides, "universal base" nucleotides, 5-C-methyl nucleotides, and inverted deoxyabasic residue incorporation (see generally GB2406568).

In another embodiment, modifications can be used to enhance the stability of the siRNA or to increase targeting efficiency. Modifications include chemical cross linking between the two complementary strands of an siRNA, chemical modification of a 3' or 5' terminus of a strand of an siRNA, sugar modifications, nucleobase modifications and/or backbone modifications, 2'-fluoro modified ribonucleotides and 2'-deoxy ribonucleotides (see generally International Publication WO2004/029212).

In another embodiment, modifications can be used to increase or decrease affinity for the complementary nucleotides in the target mRNA and/or in the complementary siNA strand (see generally International Publication WO2005/044976). For example, an unmodified pyrimidine nucleotide can be substituted for a 2-thio, 5-alkynyl, 5-methyl, or 5-propynyl pyrimidine. Additionally, an unmodified purine can be substituted with a 7-deza, 7-alkyl, or 7-alkenyl purine.

In another embodiment, when the siNA is a double-stranded siRNA, the 3'-terminal nucleotide overhanging nucleotides are replaced by deoxyribonucleotides (see generally Elbashir et al., 2001, Genes Dev, 15:188).

Demonstration of Therapeutic Utility

The compositions and methods of the invention are preferably tested in vitro, and then in vivo, for the desired therapeutic activity prior to use in humans. For example, in vitro assays which can be used to determine whether administration of a specific therapeutic protocol is indicated, include in vitro cell culture assays in which a candidate siNA is administered to cells (e.g. intestinal cells) in vitro and the effect of such protocol upon the cells is observed, e.g., decreased or inhibited expression of the target gene.

Compounds for use in therapy can be tested in suitable animal model systems prior to testing in humans, including but not limited to in rabbits, rats, mice, chicken, cows, monkeys, hamsters, etc. For example, the BALB/c mouse is the preferred standard in experimental platforms designed to study Crohn's disease. These mice are administered with a sublethal dose of TNBS (Trinitrobencene sulphonic acid) in a 50% ethanol solution. Due to the aggressiveness of this model, the ideal time-span for analysis of the disease is from 3 to 5 days after TNBS administration, as on day 7, those mice that have survived TNBS treatment have fully recovered intestines.

Therapeutic Methods

This invention encompasses methods for treating, preventing, or managing an intestinal disorder in a patient comprising administering an effective amount of one or more siNAs of the invention. In a specific embodiment, the disorder to be treated, prevented, or managed includes hyperproliferative diseases, such as colorectal cancer; autoimmune and inflammatory bowel diseases (IBD), such as Crohn's disease; colitis, in particular ulcerative colitis; irritable bowel syndrome; infectious diseases of the intestine, such as pseudomembranous colitis, amebiasis or intestinal tuberculosis; colonic polyps; diverticular disease; constipation; intestinal obstruction; malabsorption syndromes; rectal diseases and diarrhoea.

In preferred embodiments, the siNAs used in the therapeutic methods of the invention decrease or inhibit expression of genes that affect the above captioned intestinal diseases. For example, in a specific embodiment of the invention, in the case of Crohn's disease siNAs directed to IL-12 are used, this being incorporated in the present application as a specific embodiment of the present invention. In certain embodiments of said example, one or more of the siNAs of the invention are selected from the group consisting of SEQ ID NO: 1-85. In a specific preferred embodiment, the siNAs used in the therapeutic methods of the invention are dsRNA of any of SEQ ID NO: 1-85 hybridized to its complement. The invention also encompasses siNAs that are 40 nucleotides or less and comprise a nucleotide sequence of any of SEQ ID NO: 1-85 hybridized to its complement. In a specific embodiment, the siNA is 21-30 nucleotides and comprises any of SEQ ID NO: 1-85.

In preferred embodiments, the methods of the invention provide a sustained decrease in the symptoms of the intestinal disorder that last for longer than 8, 10, 12 or 14 hours, more preferably several days (e.g. 2 days, 3 days, 4 days, or 5 days), after the last administration of siNA. In such embodiments, the effect (i.e. decrease in symptom intensity and/or frequency) of administered siNAs of the invention is longer lasting than the duration of the effect of presently commercially available drugs. The siNAs of the invention that provide sustained effects can be administered in a regimen such that symptoms are continually decreased without daily administration of siNA. In a specific embodiment, a treatment regimen can include consecutive cycles of administration (e.g. one dose of siNA given daily for four days) and non-administration (e.g., 3 or 4 days with no treatment given) while still eliciting a continual decrease in symptoms.

In one embodiment, a single type of siNA is administered in the therapeutic methods of the invention. In another embodiment, a siNA of the invention is administered in combination with another siNA of the invention and/or with one or more other non-siNA therapeutic agents useful in the treatment, prevention or management of an intestinal disorder. The term "in combination with" is not limited to the administration of therapeutic agents at exactly the same time, but rather it is meant that the siNAs of the invention and the other agent are administered to a patient in a sequence and within a time interval such that the benefit of the combination is greater than the benefit if they were administered otherwise. For example, each therapeutic agent may be administered at the same time or sequentially in any order at different points in time; however, if not administered at the same time, they should be administered sufficiently close in time so as to provide the desired therapeutic effect. Each therapeutic agent can be administered separately, in any appropriate form and by any suitable route.

Dosage

As used herein, an "effective amount" refers to that amount of a siNA of the invention sufficient to treat or manage an intestinal disorder by interfering with gene expression, preferably those genes associated with increased gene expression. The effective amount sufficient to decrease symptoms. In one embodiment, the intestinal disorder is Crohn's disease whose symptoms include diarrhoea, weight loss, colon inflammation and elevated levels of TNF-α and SAA (serum amyloid antigen) in serum. A therapeutically effective amount may also refer to the amount of an siNA sufficient to delay or minimize the onset of an intestinal disorder. A therapeutically effective amount may also refer to the amount of the therapeutic agent that provides a therapeutic benefit in the treatment or management of an intestinal disorder. Further, a therapeutically effective amount with respect to an siNA of the invention means that amount of therapeutic agent alone, or in combination with other therapies, that provides a therapeutic benefit in the treatment or management of an intestinal disorder. Used in connection with an amount of an siRNA of the invention, the term can encompass an amount that improves overall therapy, reduces or avoids unwanted effects, or enhances the therapeutic efficacy of or synergizes with another therapeutic agent. Treatment with siNA alone or in combination should result in symptom reduction.

The effective amount of a composition of the invention can be determined by standard research techniques. For example, the dosage of the composition which will be effective in the treatment, prevention, attenuation, or management of the disorder can be determined by administering the composition which will be effective in the treatment, prevention or management of the disorder can be determined by administering the composition to an animal model such as, e.g. the animal models disclosed herein or known to those skilled in the art. In addition, in vitro assays may optionally be employed to help identify optimal dosage ranges. Alternatively, the dosage may be determined for an individual by titrating the dose until an effective level is reached.

Selection of the preferred effective amount to be used in dosages can be determined (e.g. via clinical trials) by a skilled artisan based upon the consideration of several factors which will be known to one of ordinary skill in the art. Such factors include the disorder to be treated or prevented, the symptoms involved, the patient's body mass, the patient's immune status and other factors known by the skilled artisan to reflect the accuracy of administered pharmaceutical compositions.

The precise dose to be employed in the formulation will also depend on the route of administration, and the seriousness of the disorder, and should be decided according to the judgment of the practitioner and each patient's circumstances. Effective doses may be extrapolated from dose-response curves derived from in vitro or animal model test systems.

Pharmaceutical Formulations and Routes of Administration.

The present invention may comprise the administration of one or more species of siNA molecule simultaneously. These species may be selected to target one or more target genes.

In one embodiment, a single type of siNA is administered in the therapeutic methods of the invention. In another embodiment, a siNA of the invention is administered in combination with another siNA of the invention and/or with one or more other non-siNA therapeutic agents useful in the treatment, prevention or management of a disease condition of the intestine wall. The term "in combination with" is not limited to the administration of therapeutic agents at exactly the same time, but rather it is meant that the siNAs of the invention and the other agent are administered to a patient in a sequence and within a time interval such that the benefit of the combination is greater than the benefit if they were administered otherwise. For example, each therapeutic agent may be administered at the same time or sequentially in any order at different points in time; however, if not administered at the same time, they should be administered sufficiently close in time so as to provide the desired therapeutic effect. Each therapeutic agent can be administered separately, in any appropriate form and by any suitable route.

The siNAs of the invention may be formulated into pharmaceutical compositions by any of the conventional techniques known in the art (see for example, Alfonso, G. et al., 1995, in: The Science and Practice of Pharmacy, Mack Publishing, Easton Pa., 19th ed.). Formulations comprising one or more siNAs for use in the methods of the invention may be in numerous forms, and may depend on the various factors specific for each patient (e.g., the type and severity of disorder, type of siNA administered, age, body weight, response, and the past medical history of the patient), the number and type of siNAs in the formulation, the form of the composition (e.g., in liquid, semi-liquid or solid form), the therapeutic regime (e.g. whether the therapeutic agent is administered over time as a slow infusion, a single bolus, once daily, several times a day or once every few days), and/or the route of administration (e.g., topical, oral, intravenous, intramuscular, intra-arterial, intramedullary, intrathecal, transdermal, subcutaneous, intraperitoneal, intranasal, enteral, or sublingual means).

The siNA molecules of the invention and formulations or compositions thereof may be administered directly or topically as is generally known in the art. For example, a siNA molecule can comprise a delivery vehicle, including liposomes, for administration to a subject. Carriers and diluents and their salts can be present in pharmaceutically acceptable formulations. Nucleic acid molecules can be administered to cells by a variety of methods known to those of skill in the art, including, but not restricted to, encapsulation in liposomes, by iontophoresis, or by incorporation into other vehicles, such as biodegradable polymers, hydrogels, cyclodextrins poly (lactic-co-glycolic) acid (PLGA) and PLCA microspheres, biodegradable nanocapsules, and bioadhesive microspheres, or by proteinaceous vectors. In another embodiment, the nucleic acid molecules of the invention can also be formulated or complexed with polyethyleneimine and derivatives thereof, such as polyethyleneimine-polyethyleneglycol-N-acetylgalactosamine (PEI-PEG-GAL) or polyethyleneimine-polyethyleneglycol-tri-N-acetylgalactosamine (PEI-PEG-triGAL) derivatives.

A siNA molecule of the invention may be complexed with membrane disruptive agents and/or a cationic lipid or helper lipid molecule.

Delivery systems which may be used with the invention include, for example, aqueous and non aqueous gels, creams, multiple emulsions, microemulsions, liposomes, ointments, aqueous and non aqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone). In one embodiment, the pharmaceutically acceptable carrier is a liposome or a transdermal enhancer.

A pharmaceutical formulation of the invention is in a form suitable for administration, e.g., systemic or local administration, into a cell or subject, including for example a human. Suitable forms, in part, depend upon the use or the route of entry, for example oral, rectal, transdermal, or by injection. Other factors are known in the art, and include considerations such as toxicity and forms that prevent the composition or formulation from exerting its effect.

The present invention also includes compositions prepared for storage or administration that include a pharmaceutically effective amount of the desired compounds in a pharmaceutically acceptable carrier or diluent. Acceptable carriers or diluents for therapeutic use are well known in the pharmaceutical art. For example, preservatives, stabilizers, dyes and flavoring agents can be provided. These include sodium benzoate, sorbic acid and esters of p-hydroxybenzoic acid. In addition, antioxidants and suspending agents can be used.

A pharmaceutically effective dose is that dose required to prevent, attenuate, inhibit the occurrence, or treat (alleviate a symptom to some extent, preferably all of the symptoms) of a disease state. The pharmaceutically effective dose depends on the type of disease, the composition used, the route of administration, the type of mammal being treated, the physical characteristics of the specific mammal under consideration, concurrent medication, and other factors that those skilled in the medical arts will recognize.

The formulations of the invention can be administered in dosage unit formulations containing conventional non-toxic pharmaceutically acceptable carriers, adjuvants and/or vehicles. Formulations can be in a form suitable for oral use, for example, as tablets, troches, lozenges, aqueous or oily suspensions, dispersible powders or granules, emulsion, hard or soft capsules, or syrups or elixirs. Compositions intended for oral use can be prepared according to any method known to the art for the manufacture of pharmaceutical compositions and such compositions can contain one or more such sweetening agents, flavoring agents, coloring agents or preservative agents in order to provide pharmaceutically elegant and palatable preparations. Tablets contain the active ingredient in admixture with non-toxic pharmaceutically acceptable excipients that are suitable for the manufacture of tablets.

These excipients can be, for example, inert diluents; such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets can be uncoated or they can be coated by known techniques. In some cases such coatings can be prepared by known techniques to delay disintegration and absorption in the gastrointestinal tract and thereby provide a sustained action over a longer period. For example, a time delay material such as glyceryl monostearate or glyceryl distearate can be employed.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in a mixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents and flavoring agents can be added to provide palatable oral preparations. These compositions can be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present.

Pharmaceutical compositions of the invention can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

Syrups and elixirs can be formulated with sweetening agents, for example glycerol, propylene glycol, sorbitol, glucose or sucrose. Such formulations can also contain a demulcent, a preservative, and flavoring and coloring agents. The pharmaceutical compositions can be in the form of a sterile injectable aqueous or oleaginous suspension.

This suspension can be formulated according to the known art using those suitable dispersing or wetting agents and suspending agents that have been mentioned above.

A sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid find use in the preparation of injectables.

The nucleic acid molecules of the invention can also be formulated for rectal administration, e.g., in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Nucleic acid molecules of the invention can be administered parenterally in a sterile medium. The drug, depending on the vehicle and concentration used, can either be suspended or dissolved in the vehicle. Advantageously, adjuvants such as local anaesthetics, preservatives and buffering agents can be dissolved in the vehicle.

For administration to non-human animals, the composition can also be added to the animal feed or drinking water. It can be convenient to formulate the animal feed and drinking water compositions so that the animal takes in a therapeutically appropriate quantity of the composition along with its diet. It can also be convenient to present the composition as a premix for addition to the feed or drinking water.

The nucleic acid molecules of the present invention can also be administered to a subject in combination with other therapeutic compounds to increase the overall therapeutic effect. The use of multiple compounds to treat an indication can increase the beneficial effects while reducing the presence of side effects.

Alternatively, certain siNA molecules of the invention can be expressed within cells from eukaryotic promoters. Recombinant vectors capable of expressing the siNA molecules can be delivered and persist in target cells. Alternatively, vectors can be used that provide for transient expression of nucleic acid molecules. Such vectors can be repeatedly administered as necessary. Once expressed, the siNA molecule interacts with the target mRNA and generates an RNAi response. Delivery of siNA molecule expressing vectors can be systemic, such as by intravenous or intra-muscular administration, by administration to target cells ex-planted from a subject followed by reintroduction into the subject, or by any other means that would allow for introduction into the desired target cell.

The contents of all published articles, books, reference manuals and abstracts cited herein, are hereby incorporated by reference in their entirety to more fully describe the state of the art to which the invention pertains.

As various changes can be made in the above-described subject matter without departing from the scope and spirit of the present invention, it is intended that all subject matter contained in the above description, or defined in the appended claims, be interpreted as descriptive and illustrative of the present invention. Modifications and variations of the present invention are possible in light of the above teachings.

EXAMPLES

It is understood that the following examples and embodiments described herein are for illustrative purposes only and that various modifications or changes in light thereof will be suggestive to persons skilled in the art and are to be included within the spirit and purview of this application and the scope of the appended claims. All publications, patents, and patent applications cited herein are hereby incorporated by reference in their entirety for all purposes.

Example 1

Design of siNA

GenBank Accession numbers corresponding to IL-12 p35 (Interleukin 12A, natural killer cell stimulatory factor 1, cytotoxic lymphocyte maturation factor 1, p35) and p40 (Interleukin 12B, natural killer cell stimulatory factor 2, cytotoxic lymphocyte maturation factor 2, p40) subunits are NM_000882 and NM_002187, respectively.

Corresponding mRNA nucleotide sequences were introduced within the proprietary prediction program described above, and siNA molecules directed to target IL-12 p35 and p40 subunits were obtained. The output of this analysis was a score of possible siNA oligonucleotides, the highest scores being used to design double stranded RNA oligonucleotides (typically 19 bp long) that were typically made by chemical synthesis.

In preferred embodiments, siNA compositions of the invention are any of SEQ ID NOS: 1-85 of FIG. 1; typically administered as a duplex of the sense strand and the antisense strand. The invention also encompasses siNA that are 40 nucleotides or less and comprise a nucleotide sequence of any of SEQ ID NOS: 1-85. In a specific embodiment, the siNA is 21-30 nucleotides long and comprises any one of SEQ ID NOS:1-85 of FIG. 1. All siNA molecules used in the experiments described below were designed to have a 2 thymidine nucleotide 3' overhang, their length therefore being of 21 nucleotides.

Example 2

In Vitro Assays

To check the specificity of the siRNA interference, cell cultures expressing the target genes were employed.

In the case of IL-12 p35 and p40 subunits, the cells used for the experiments were human colon adenocarcinoma SW480 cells and murine muscle cells C2C12. After incubation of the cells with the corresponding siRNA duplexes, the levels of p35 and p40 expression were analyzed. For linking siRNA knockdown to specific phenotypes in cultured cells, it is necessary to demonstrate the decrease of the targeted protein or at least to demonstrate the reduction of the targeted mRNA.

mRNA levels of the target gene can be quantitated by real time PCR (RT-PCR). Further, the protein levels can be determined in a variety of ways well known in the art, such as Western blot analysis with specific antibodies to the different target allow direct monitoring of the reduction of targeted protein.

siRNA are introduced into cells by means of any transfection technique well known in the art. A single transfection of siRNA duplex can be performed, for instance, by using a cationic lipid, such as Lipofectamine 2000 Reagent (Invitrogen), followed by an assay of silencing efficiency 24, 48 and 72 hours after transfection.

A typical transfection protocol can be performed as follows: for one well of a 6-well plate, we transfect using 100 nM for murine C2C12 cells or 200 nM for human SW480 cells as final concentration of siRNA. Following Lipofectamine 2000 Reagent protocol, the day before transfection, we seed 2-4× $10^5$ cells per well in 3 ml of an appropriate growth medium, containing DMEM, 10% serum, antibiotics and glutamine, and incubate cells under normal growth conditions (37° C. and 5% $CO_2$). On the day of transfection, cells have to be at 30-50% confluence. We dilute 12.5 µl of 20 µM siRNA duplex (corresponding to 100 nM final concentration) or 25 µl of 20 µM siRNA duplex (corresponding to 200 nM final concentration) in 250 µl of DMEM and mix. Also, 6 µl of Lipofectamine 2000 is diluted in 250 µl of DMEM and mixed. After 5 minutes incubation at room temperature, the diluted oligomer (siRNA duplex) and the diluted Lipofectamine are combined to allow complex formation during 20 minutes incubation at room temperature. Afterwards, we add the complexes drop-wise onto the cells with 2 ml of fresh growth medium low in antibiotics and mix gently by rocking the plate back and forth, to ensure uniform distribution of the transfection complexes. We incubate the cells under their normal growth conditions and the day after, the complexes are removed and fresh and complete growth medium is added. To monitor gene silencing, cells are collected at 24, 48 and 72 h post-transfection.

The efficiency of transfection may depend on the cell type, but also on the passage number and the confluency of the cells. The time and the manner of formation of siRNA-liposome complexes (e.g. inversion versus vortexing) are also critical. Low transfection efficiencies are the most frequent cause of unsuccessful silencing. Good transfection is a non-trivial issue and needs to be carefully examined for each new cell line to be used. Transfection efficiency may be tested transfecting reporter genes, for example a CMV-driven EGFP-expression plasmid (e.g. from Clontech) or a B-Gal expression plasmid, and then assessed by phase contrast and/or fluorescence microscopy the next day.

Depending on the abundance and the life time (or turnover) of the targeted protein, a knock-down phenotype may become apparent after 1 to 3 days, or even later. In cases where no phenotype is observed, depletion of the protein may be observed by immunofluorescence or Western blotting.

After transfections, total RNA fractions extracted from cells are pre-treated with DNase I and used for reverse transcription using a random primer. PCR-amplified with a specific primer pair covering at least one exon-exon junction is used as control for amplification of pre-mRNAs. RT-PCR of a non-targeted mRNA is also needed as control. Effective depletion of the mRNA yet undetectable reduction of target protein may indicate that a large reservoir of stable protein may exist in the cell. Alternatively, RT-PCR amplification can be used to test in a more precise way the mRNA decrease or disappearance. RT-PCR quantitates the initial amount of the template most specifically, sensitively and reproducibly. RT-PCR monitors the fluorescence emitted during the reaction as an indicator of amplicon production during each PCR cycle, in a light cycler apparatus. This signal increases in direct proportion to the amount of PCR product in a reaction. By recording the amount of fluorescence emission at each cycle, it is possible to monitor the PCR reaction during exponential phase where the first significant increase in the amount of PCR product correlates to the initial amount of target template.

To verify the interference pattern of the differentially expressed IL-p35 and p40 genes in the cell cultures, quantitative RT-PCR was performed. For quantitative RT-PCR, approximately 500 ng of total RNA was used for reverse transcription, followed by PCR amplification with specific primers for each gene in reaction. The PCR conditions were an initial step of 30 s at 95° C., followed by 40 cycles of 5 s at 95° C., 10 s at 62° C. and 15 s at 72° C. Quantification of 18S mRNA was used as a housekeeping gene as a control for data normalization. Relative gene expression comparisons work best when the gene expression of the chosen endogenous/internal control is more abundant and remains constant, in proportion to total RNA, among the samples. By using an invariant endogenous control as an active reference, quantitation of an mRNA target can be normalized for differences in the amount of total RNA added to each reaction. The amplification curves obtained with the light cycler were analyzed in combination with the control kit DNA, which targets in vitro transcribed beta-globin DNA template, according to the manufacturer protocol. In order to assess the specificity of the amplified PCR product a melting curve analysis was performed. The resulting melting curves allow discrimination between primer-dimers and specific PCR product.

Example 2.1

In Vitro Assays for IL-12 p35

To determine the inhibition of the IL-12 p35 target gene, a panel of siRNA contained within FIG. 1 were analyzed in cell cultures. siRNA with the best characteristics were selected to be tested and were applied to proper cell cultures, such as SW480. The effect of siRNA over the target gene was analyzed by RT-PCR according to the manufacturer's protocol. The gene target transcript levels were normalized using 18S as a housekeeping gene. Some of the different siRNA that were tested and their different efficacies in the interference of the target gene are included in the FIG. 2. These results correspond to transfection of 21-mer siNAs containing SEQ ID NO: 8 or SEQ ID NO: 17 in SW480 cells which naturally express IL-12p35. The values represent the mean of the percentage of the normalized mRNA levels upon siRNA interference over the control gene expression and their medium standard deviations (SEM). The level of p35 transcript after siRNA treatment was highly reduced with siRNAs corresponding to SEQ ID NO: 8 and SEQ ID NO: 17, when compared to the control cells. The decrease in gene expression depends on the efficiency of siRNA silencing. In fact, siRNA SEQ ID NO: 8 treatment decreased p35 gene expression to 56% at 24 h compared to the control expression levels.

Example 3

In Vitro Assays for IL-12 p40

To determine the inhibition of the IL-12 p40 target gene, a panel of siRNA contained in FIG. 1 was analyzed. The siRNA with the best characteristics designed as described previously, were tested in human and murine cells. The p40 transcript level was analyzed by RT-PCR and normalized using 18S as a housekeeping gene. These results correspond to SEQ ID NO: 67 and SEQ ID NO: 79 in SW480 human cells which naturally express IL-12p40 (FIG. 3A); and SEQ ID NO: 86 and SEQ ID NO: 87 in C2C12 murine cells which naturally express IL-12p40 (FIG. 3B). siNA molecules used in the present experiment were as described in FIG. 1 to which 2 thymidine nucleotide 3' overhangs were added.

The level of p40 transcript was highly reduced after treatment with siRNA corresponding to SEQ ID NO: 67 in SW480 cells, up to 65% at 24 h compared to control cells. In C2C12 cells siRNA corresponding to SEQ ID NO: 86 decreased gene expression to 61% at 48 h compared to the control cells. It is important to note that SEQ ID NO: 67 and SEQ ID NO: 86 correspond to homologous regions of human and mouse IL-12 p40 gene, respectively.

The same experiments were carried out using RAW cell line, which are mouse macrophages, with similar results.

A summary of the experiments of FIGS. 2 and 3 is displayed in Table 1.

TABLE 1

|  |  | Gene expression (%) | SEM |
| --- | --- | --- | --- |
| P35 (SW480) | Control | 100 | 0 |
|  | SEQ ID 8, 24 h | 56 | 13.9772455 |
|  | SEQ ID 8, 48 h | 73 | 13.6336806 |

TABLE 1-continued

|  |  | Gene expression (%) | SEM |
| --- | --- | --- | --- |
|  | SEQ ID 17, 24 h | 67 | 17.8860754 |
|  | SEQ ID 17, 48 h | 73 | 20.7305043 |
| p40 (SW480) | Control | 100 | 0 |
|  | SEQ ID 67, 24 h | 65 | 8.58321816 |
|  | SEQ ID 67, 48 h | 86 | 20.4353968 |
|  | SEQ ID 79, 24 h | 69 | 17.8276602 |
|  | SEQ ID 79, 48 h | 84 | 13.1055338 |
| p40 (C2C12) | Control | 100 | 0 |
|  | SEQ ID 86, 24 h | 121 | 13.8703694 |
|  | SEQ ID 86, 48 h | 61 | 23.4419624 |
|  | SEQ ID 87, 24 h | 108 | 35.8061452 |
|  | SEQ ID 87, 48 h | 85 | 17.1974522 |

Example 4.1

In Vivo Assays: Intrarectal Administration of siNA

Intrarectal siNA delivery studies were carried out in GFP C57BL/6-TG (ACTB-EGFP) mice. This transgenic mouse line was bought from "The Jackson Laboratory". Transgenic mice have been used because homozygous mice for this transgene die within the first two weeks following birth. The transgenic mouse line with an "enhanced" GFP (EGFP) cDNA under control of a chicken beta-actin promoter and cytomegalovirus enhancer makes all of the tissues, with the exception of erythrocytes and hair, appear green under excitation light. This strain was generated in C57BL/6 mice. The strain cDNA encoding enhanced green fluorescent protein (EGFP) was adjoined to the chicken beta actin promoter and cytomegalovirus enhancer. A bovine globin polyadenylation signal was also included in the construct. The EcoRI sites included in the PCR primers were used to introduce the amplified EGFP cDNA into a pCAGGS expression vector containing chicken beta-actin promoter and cytomegalovirus enhancer, beta-actin intron and bovine globin poly-adenylation signal. The entire insert with the promoter and coding sequence was excised with Bam-HI and SalI and gel-purified.

The siRNA duplex used for intrarectal injection in mice was purchased from Dharmacon. Dharmacon Research Inc (Lafayette, Colo.) have developed a new generation of modified siRNA for in vivo use as a therapeutic, named siSTABLEv2. Dharmacon's siSTABLEv2 siRNA have demonstrated a enhanced stability in serum with respect to that of non-modified siRNA. Conventional siRNA are typically degraded within minutes in serum-containing environments, making in vivo use of siRNA problematic. The siSTABLEv2 modification dramatically extends the siRNA stability in serum.

The siRNA used to downregulate EGFP mRNA expression targeted the following sequence in EGFP mRNA: 5'-GGC UAC GUC CAG GAG CGC ACC-3' (SEQ ID NO: 88). The sense strand of the siRNA duplex was 5'-P GGC UAC GUC CAG CGC ACC-3' (SEQ ID NO: 89) and the antisense strand was 5'-P U GCG CUC CUG GAC GUA GCC UU-3' (SEQ ID NO: 90). This sequence is distributed by Dharmacon as pre-synthesized control siRNA green fluorescent protein duplex.

For the intrarectal delivery experiments C57BL/6-TG (ACTB-EGFP) mice (males, 8 weeks old) were used. The animals were kept in cages with free access to food and water until one day before the experimental protocol. For intrarectal therapeutic silencing, mice were fasted for one day prior to treatment. The drugs are typically administered by injecting a small volume (120 µL) in the rectum. Control mouse is treated with the vehicle alone. In all cases animals were sacrificed two days after the first injection by cervical dislocation. The protocol for siRNA application in mice is as follows. For each experimental administration, 60 μl siRNA duplexes were premixed with 60 μl of NaCl (1.8% w/v) up to physiological levels. In all cases animals were sacrificed two days after the first injection.

Experimental conditions used are indicated in the Table below. Each condition was analyzed in duplicate. Mice 2 and 3 were treated intrarectally with one dose of 250 μg (19 nanomols) of the siRNA against GFP, while mice 4 and 5 were treated with two doses of 125 μg of siRNA during two consecutive days. Table 2 provides a schematic distribution of experimental conditions for intrarectal siRNA delivery. Doses of siRNA are indicated in the table.

TABLE 2

| Mouse number | Intrarectal Therapeutic Treatment |
| --- | --- |
| 1 | Vehicle control dose |
| 2 | Single dose of 250 μg of siRNA |
| 3 | Single dose of 250 μg of siRNA |
| 4 | Two doses of 125 μg of siRNA with a 24 h interval |
| 5 | Two doses of 125 μg of siRNA with a 24 h interval |

The sample tissues were collected and analyzed by two methods: One in OCT medium and another in RNA LATER® (Ambion). OCT blocks were stored at −80° C. until data processing. OCT blocks were cut in slices of 12 μm using a cryostat (Leica CM 1850) at −20° C. The collected slices were analyzed on a fluorescence microscope (Olympus BX51) coupled to a digital camera (DP70), using a filter of 488 nm. The sensitivity conditions (180200), resolution image size (2040×1536) and time exposure (1 second) were set up for all samples in order to be compared among them. Green fluorescence was measured as an index of GFP expression by an Adobe PHOTOSHOP® program (version 8.0). By this method, 25 different data were collected for each analyzed tissue. Tissues isolated in RNA LATER® were stored at −20° C. RNA LATER® was removed before RNA extraction. RNA was isolated with the Tryzol Reagent (Invitrogen) according to the manufacturer protocol. DNAse treatment was done before measurement of GFP expression by RT-PCR as described above.

Example 4.2

In Vivo Assays. Analysis of the Small Intestine

The siRNA application is made in order to determine proper siRNA delivery to the intestine. To determine siRNA effect, small intestine samples were collected in OCT medium and analyzed as previously described. Since the goal is to determine the downregulation of GFP gene transcript, levels of fluorescence were measured following siRNA application. No secondary effects were observed in the animals during the experimental protocols.

Figure 4:
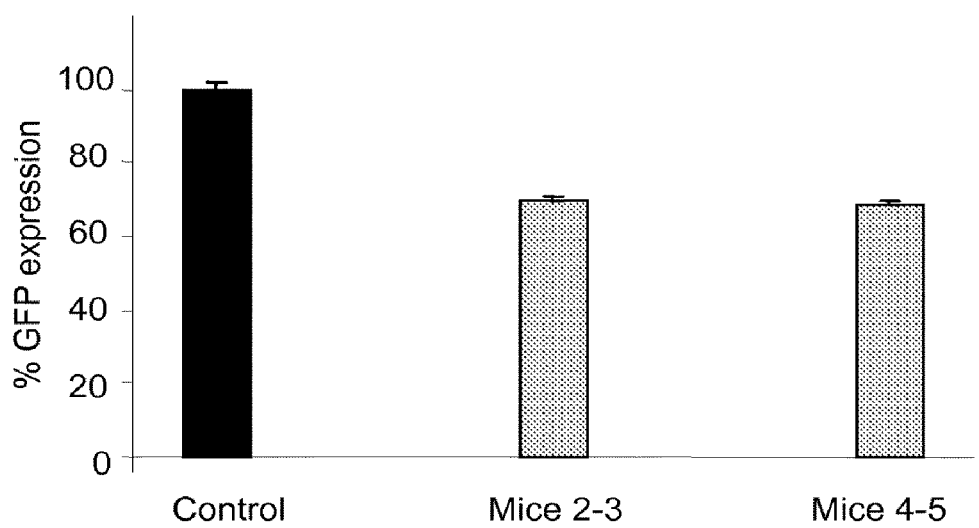
FIG. 4: siRNA treatment reduces the levels of GFP gene transcript in small intestine. The collected tissue in OCT was analyzed by microscopy and measured by PHOTOSHOP® program. Data show single dose siRNA treatment (mice 2-3) and repeated dose treatment (mice 4-5). The values show the expression levels of 25 representative images per mouse referred to control untreated mouse. Standard deviation of the data is represented.

The first work group (animals 2 and 3) was treated with a single dose of 250 μg of siRNA and sacrificed 48 h later. The results indicate a significant decrease of fluorescence when compared with the control mouse. Moreover, when the siRNA (250 μg) is administered in two doses of 125 μg and analyzed 48 h after the first injection, the decrease of GFP expression was similar to that after a single application. The results are shown in FIG. 4. For each experimental condition an average of the data is represented.

At the same time, small intestine samples were collected in RNA LATER® to confirm previous data. mRNA levels were measured by RT-PCR. These results, shown in FIG. 5, confirm the previous ones obtained with fluorescence analysis.

Figure 5:
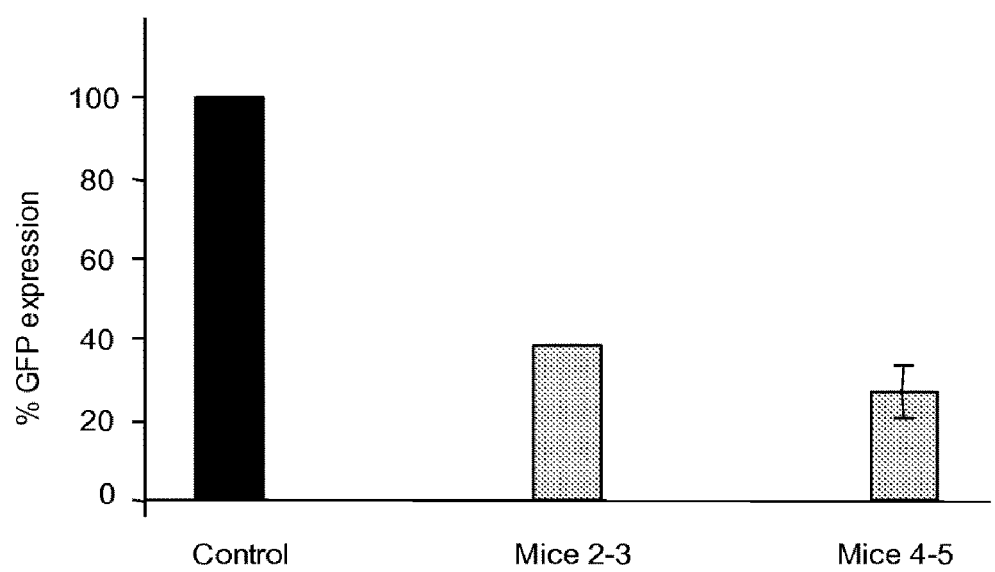
FIG. 5: siRNA treatment reduces the levels of GFP gene transcript in small intestine. The tissue collected in RNA LATER® was analyzed by RT-PCR. Data show single dose siRNA treatment (mice 2-3) and repeated dose treatment (mice 4-5). Standard deviation is represented.

As shown in FIG. 5, the administered dose of 250 μg of siRNA in one or two applications was enough and sufficient to downregulate the level of GFP mRNA in small intestine, confirming the efficient delivery of siRNA in small intestine by intrarectal administration. The level of downregulation compared to control mice is higher when the analysis is carried out by RT-PCR due to the higher sensitivity of the technique Example 4.3

In Vivo Assays. Analysis of Large Intestine

Figure 6:
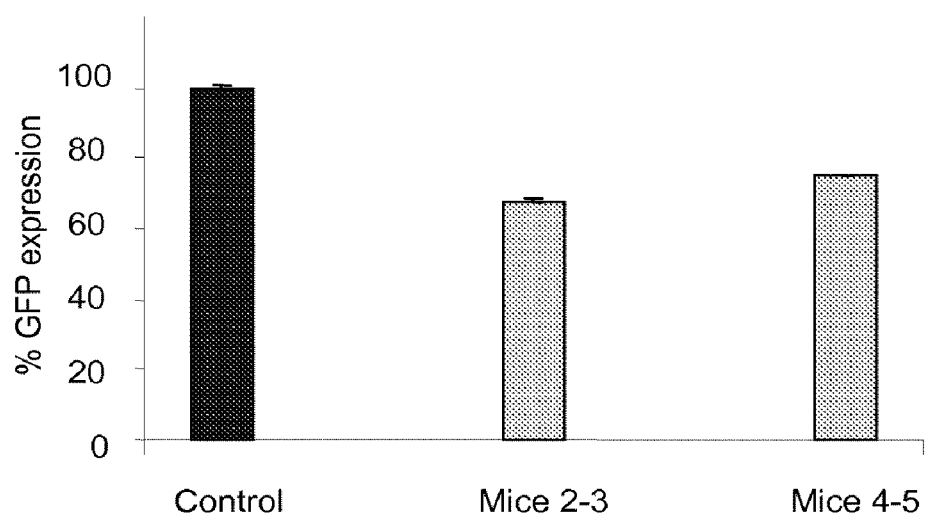
FIG. 6: siRNA treatment reduces the levels of GFP gene transcript in large intestine. The tissue collected in OCT was analyzed by microscopy and measured by PHOTOSHOP® program. Data show single dose siRNA treatment (mice 2-3) and repeated dose treatment (mice 4-5). The values show the expression levels of 25 representative images per mouse referred to control untreated mouse. Standard deviation of the data is represented.

Large intestine was further analyzed in the same way as small intestine. To determine siRNA effect in large intestine, samples collected in OCT medium were analyzed to determine GFP downregulation by measurement of fluorescence following siRNA application. The results indicate a significant decrease of fluorescence when compared to control mouse (FIG. 6). Moreover, when the dose is administered in two applications of 125 μg and analyzed 48 h after the first injection, the decrease was very similar to that obtained after a single siRNA administration, demonstrating the effectiveness of the treatment.

Figure 7:
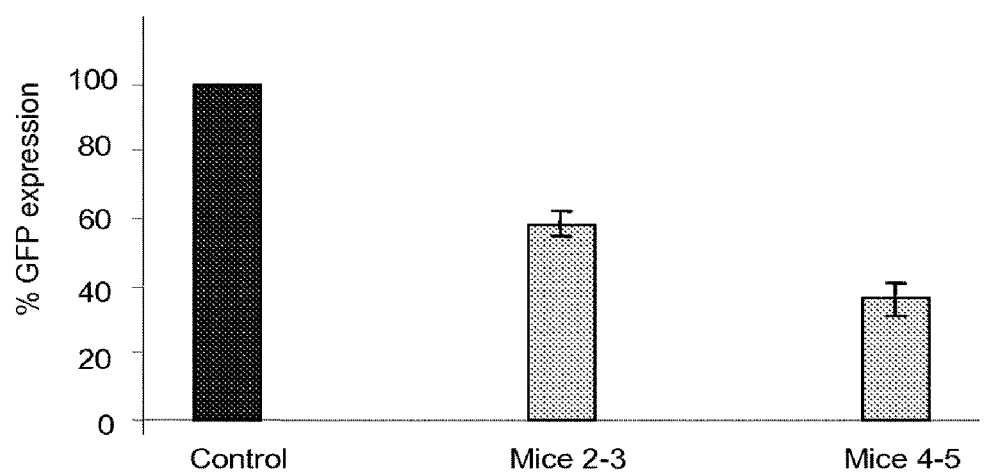
FIG. 7: siRNA treatment reduces the levels of GFP gene transcript in large intestine. The collected tissue in RNA LATER® was analyzed by RT-PCR. Data show single dose siRNA treatment (mice 2-3) and repeated dose treatment (mice 4-5). Standard deviation is represented.

As in small intestine, large intestine samples were collected in RNA LATER® and data of mRNA levels represented in FIG. 7. The data obtained by RT-PCR confirm the previous ones obtained with fluorescence analysis. These results open a new route to therapeutic siRNA administration to treatment of bowel diseases.

Data of samples collected in OCT medium and in RNA LATER® are summarized in FIGS. 8 and 9 respectively.

Downregulation of GFP expression in other selected tissues of the mice was also analyzed: no downregulation was observed in bladder, kidney, lung, ovary, or liver tissues, suggesting that intrarectal administration of siRNA can be used to specifically target intestinal tissue.

Example 5

In Vivo Analysis of the Effects of IL-12 Specific siRNA Intrarectal Administration on Crohn's Disease The experiments described below were performed on a murine model of Crohn's disease, and is described in detail in the following paragraphs.
Materials & Methods
Colitis Induction Colitis was induced by intrarectal administration of TNBS (Trinitrobencene sulphonic acid; Sigma Chemical Co., St. Louis, Mo.) following standard procedures well known to those field experts who are familiar with creating murine models for Crohn's disease. In brief, 120 μl of a solution containing 3 mg of TNBS dissolved in a 50% ethanol solution, were injected in male BALB/c mice previously anesthetized with halothane (8 weeks old; Jackson Laboratories, Bar Harbor, Me.), using a catheter carefully inserted 4 cm from the anus. Next, animals were maintained in a vertical position for 30 seconds and returned to cages. Following the same method, a control group of animals received 120 μl of a 50% ethanol solution.

Treatment and Colitis Monitoring Protocols

IL-12p40 specific siRNA used in the present example has the following sequence:

```
5'-CUACAGCACCAGCUUCUUC-3'    (SEQ ID NO: 91)

3'-GAUGUCGUGGUCGAAGAAG-5'    (SEQ ID NO: 96)
```

This sequence being the murine homologue to SEQ ID NO: 67 where mismatches are shown in bold underlined script.

One group of animals received an only dose of 250 µg of IL-12p40 specific siRNA, dissolved in 120 µl of NaCl, 12 hours after TNBS administration. The other group received two doses of siRNA, each of 125 µg in 120 µl; the first was administered 3 hours, and the second 12 hours, after induction of colitis. In all cases administration was intrarectal. Control animals received in the same manner an only dose, or two doses of NaCl (120 µl) 12 hours, and 3 and 12 hours after TNBS administration, respectively Animals previously injected with TNBS or with 50% ethanol, also received a dose of NaCl 12 hours later.

Body weight was measured on a daily basis and used as an indicator of colitis progression, degree of colitis was established using values from 0 (no signs of colitis) to 4 (severe colitis). The person performing this analysis did not know the treatment each animal had received.

Figure 10A:
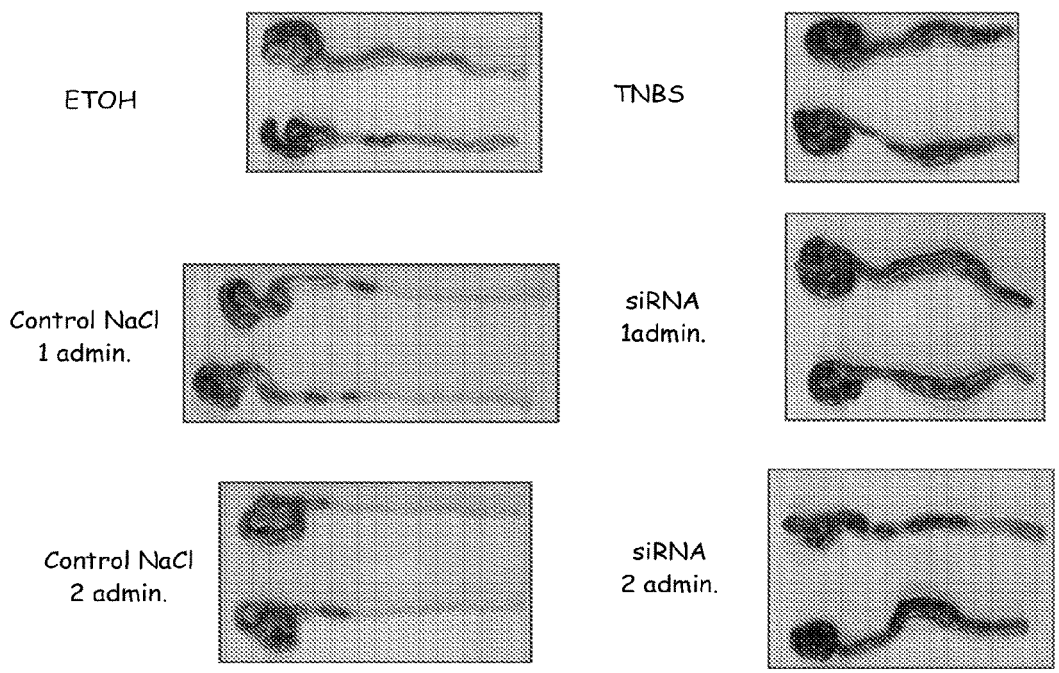
FIGS. 10A-10C: Analysis of colon macroscopic morphology in a murine model of Crohn's disease. (A) Photographs showing colon macroscopic morphology at day 3 after TNBS administration. Note severe necrosis of TNBS sample in comparison to controls having received EtOH or NaCl. Note also that degree of necrosis is decreased in individuals treated with IL-12p40 siRNA, especially those who have received 2 doses. (B) Colon macroscopic morphology on day 5 after TNBS administration. As may be observed, recovery in IL-12p40 siRNA treated individuals is clearly apparent over their TNBS counterparts. (C) Colon macroscopic morphology on day 7. Note colon recovery almost to control levels in all treatments, i.e., TNBS and IL-12p40.
Figure 10B:
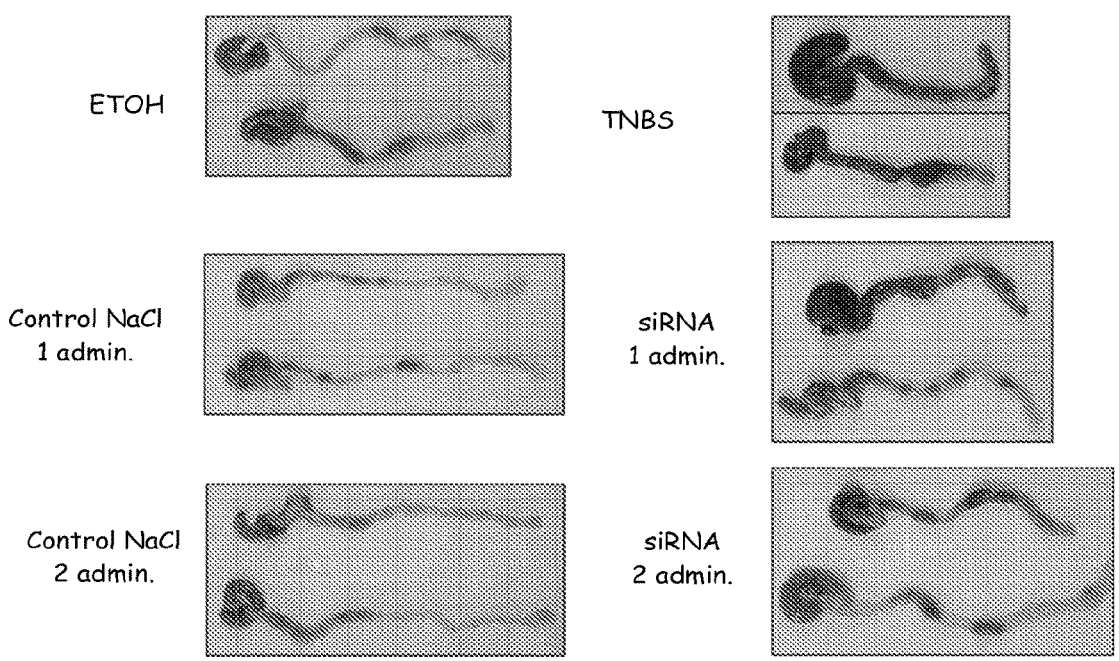
Figure 10C:
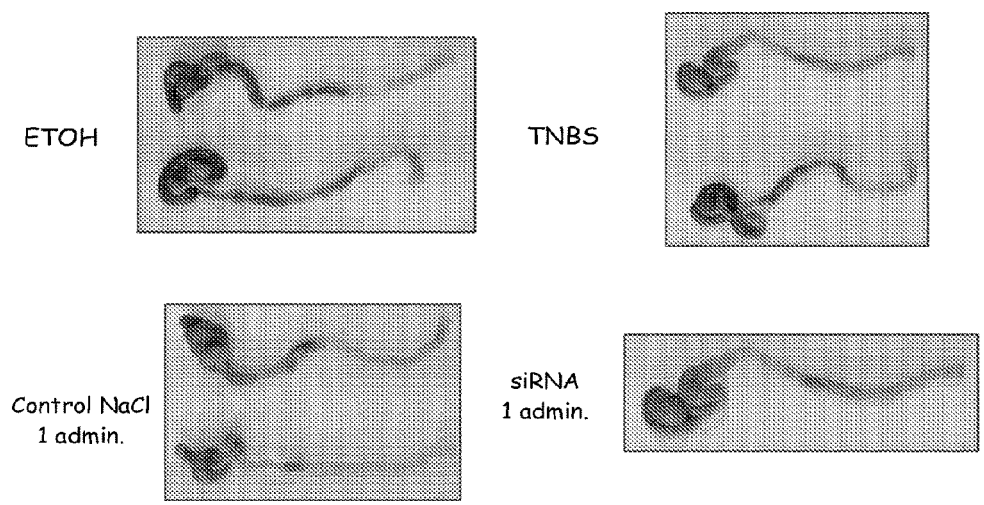

Also survival was analyzed and monitored for 7 days. As indicated previously and as is shown in the present results, the ideal time span for Crohn's disease analysis in this model is between days 3 and 5 post-injection. The reason for this time span being due to the fact that TNBS is administered at a sublethal dose wherein those mice that have survived to day 7 show a fully recovered intestine (FIG. 10).

Hystopathological Analysis

Colons were recovered 3, 5 and 7 days after TNBS administration, fixed in Bouin solution and included in paraffin. 7 µm sections were obtained and dyed with ingrain blue/hemalum/picricindigocarmine or hematoxillin/eosin using standard techniques. Inflammation was measured by a person without previous knowledge concerning the experimental group under analysis, assigning a value from 0 to 4 according to the following: 0, no signs of inflammation; 1, scant leukocyte infiltration of lamina propria; 2, moderate leukocyte infiltration and some fibrosis; 3, high leukocyte infiltration, moderate fibrosis and loss of goblet cells; and 4, massive loss of goblet cells, extensive fibrosis, colon wall reduction and epithelium breakage.

Determination of Serum Levels of Tumour Necrosis Factor-α (TNF-α) and Serum Amyloid A (SAA) by ELISA.

Serum was extracted from blood samples obtained by cardiac puncture on days 3, 5 and 7 and stored at −20° C. until TNF-α and SAA analysis. Serum TNF-α levels were measured by ELISA using a commercial kit (Mouse TNF ELISA Kit II; BD Biosciences, San Diego, Calif.) following manufacturer's instructions, except that sample and standard incubation was performed overnight at 4° C. instead of 2 hours at room temperature.

To determine serum levels of SAA, a mouse ELISA kit was used (Tridelta Development, Wicklow, Ireland) following manufacturer's instructions. Optimal serum dilution was determined previously for SAA analysis in each group.

Obtaining Total RNA.

The colon (the half that is closest to the cecum) and mesenteric lymph nodes were extracted from mice and homogenized in 1 ml Ultraspec™ (Biotecx, Houston, Tex.). The resulting lysate was incubated for 5 minutes on ice to ensure complete disassociation of nucleoprotein complexes, and RNA was extracted by high density centrifugation. For this purpose, 200 µl of chloroform per ml of Ultraspec were added, the mixture was vortexed for 15 seconds and kept on ice for 5 minutes. After centrifugation at 12000 g for 15 minutes, superior aqueous phase containing RNA, was separated from the interphase and lower organic phase where DNA and proteins from lysed cells are found. Next, extracted RNA was precipitated using the same volume of cold isopropanol as that of aqueous solution; the samples were kept on ice for 15 minutes and were then centrifuged for 15 minutes at 12000 g. The resulting white precipitate was washed several times with 1 ml of cold 75% ethanol, resuspended and centrifuged for 5 minutes at 7500 g in each wash. Finally, the precipitate was left to dry and resuspended in 100 µl of DEPC water for mesenteric lymph node samples and 200 µl for intestine samples. RNA was quantified by spectrophotometry (NanoDrop™ ND-1000), bearing in mind Abs 260/280 ratio.

Real Time Retrotranscription and Polymerase Chain Reaction (RT-PCR)

RT-PCR was performed using a commercial kit for real time enzymatic reaction (SYBR™ Green PCR Master Mix Applied Biosystems, Foster City, Calif.) and intestine and mesenteric lymph node samples isolated from mice. Reactions were performed in a total volume of 20 µl (with 40 ng of RNA, 10 µl of SYBR™ Green reagent, 5 U of MultiScribe retrotranscriptase, 10 µl of RNAse inhibitors (8 U) and 0.1 µl of primers (Forward and Reverse). Table shows the sequences of the primers.

TABLE 3

| Amplified gene | Primer sequence (5'→3') | GenBank accesion number (NCBI) | Amplified fragment size (5'→3') |
|---|---|---|---|
| β-Actin | for: AGAGGGAAATCGTGCGTGAC (SEQ ID NO: 92) rev: CAATAGTGATGACCTGGCCGT (SEQ ID NO: 93) | NM 007393 | 137 |
| IL-12p40 | for: GGAAGCACGGCAGCAGAATA (SEQ ID NO: 94) rev: AACTTGAGGGAGAAGTAGGAATGG (SEQ ID NO: 95) | NM 86671 | 180 |

Amplifying conditions were as follows:
30 minutes at 48° C.
10 minutes at 95° C.
40 cycles: 15 seconds at 95° C. and 1 minute at 60° C.

To perform relative quantification of gene expression, a method was used to compare the normalised quantity of mRNA of each sample, to an endogenous reference; in this case β-actin gene was used as a control, as its expression is constitutive. The formula used for this method was $2^{-\Delta\Delta Ct}$, which represents differential expression of a specific gene in a mouse sample with respect to its endogenous control. $\Delta Ct$ is the difference between Ct values of IL12p40 with respect to β-actin mRNA expression in each sample; and $\Delta\Delta Ct$ represents the difference between $\Delta Ct$ of each sample and its control (from mice treated with two doses of NaCl).

Statistical Analysis

Statistical significance was determined using Student t test and ANOVA test with GraphPad Prism software, with a significance level of * ($p<0.05$),  ($p<0.01$) and * ($p<0.001$).

Results
Colitis was induced by intrarectal administration of TNBS which produces haptenisation of colon proteins with trinitrobenzene. Experimental groups received intrarectally 1 or 2 doses of IL-12p40 siRNA intrarectally as described in the previous section.

1. SURVIVAL

Figure 11:
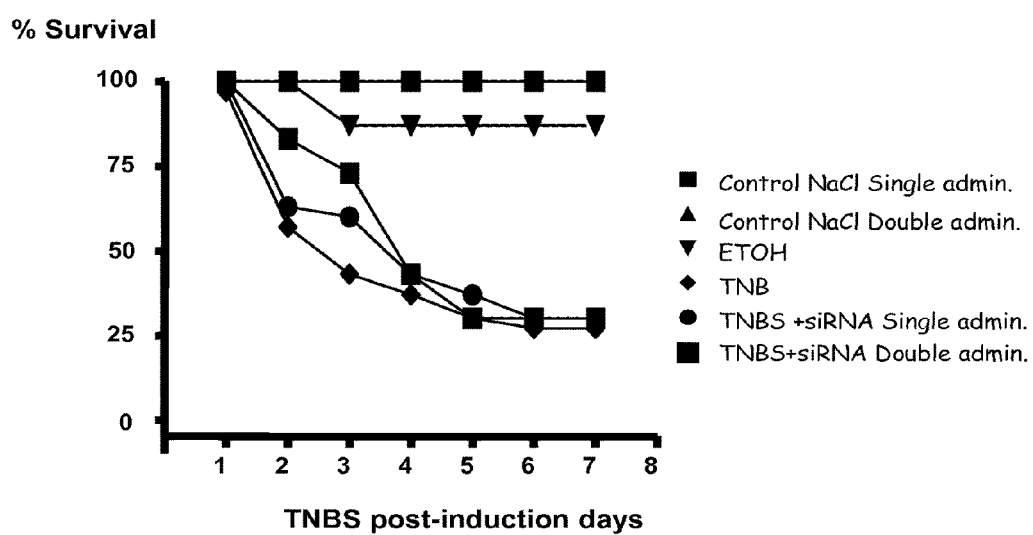
FIG. 11: The diagram shows the survival rate of mice having received one of the following treatments: a single application of NaCl 0.9%, two applications of NaCl 0.9%, one application of ethanol 50%, one application of TNBS in a 50% ethanol solution, one application of TNBS followed 12 hours later by a single application of 250 μg of IL-12p40 siRNA, or one application of TNBS followed by two applications of 125 μg of IL-12p40 siRNA, 3 and 12 hours after TNBS administration. All applications were performed in a 120 μl volume.

Analysis of survival after TNBS administration showed a very high mortality. Survival was increased after IL-12p40 siRNA administration, the peak being observed at 3 days after two administrations, representing approximately double when compared to animals treated with TNBS (see FIG. 11).

2. WEIGHT AND DEGREE OF COLITIS

After TNBS administration a drastic weight loss was observed up to day 5, recovery being observed on day 7 after TNBS administration. Mice treated with IL-12p40 siRNA behaved, as far as weight is concerned, in the same manner as those treated with TNBS.

Weight loss was accompanied by massive pancolitis which was not observed in control mice. No recovery was observed in mice treated with one or two doses of siRNA.

The fact that survival rates are not enormously increased, and that no differences are observed regarding weight loss and degree of colitis, is thought to be due to the acute inflammatory character of the model. However, as is shown below there is a notable improvement in many of the parameters associated with Crohn's disease.

3. COLON MACROSCOPIC ANALYSIS

Figure 12:
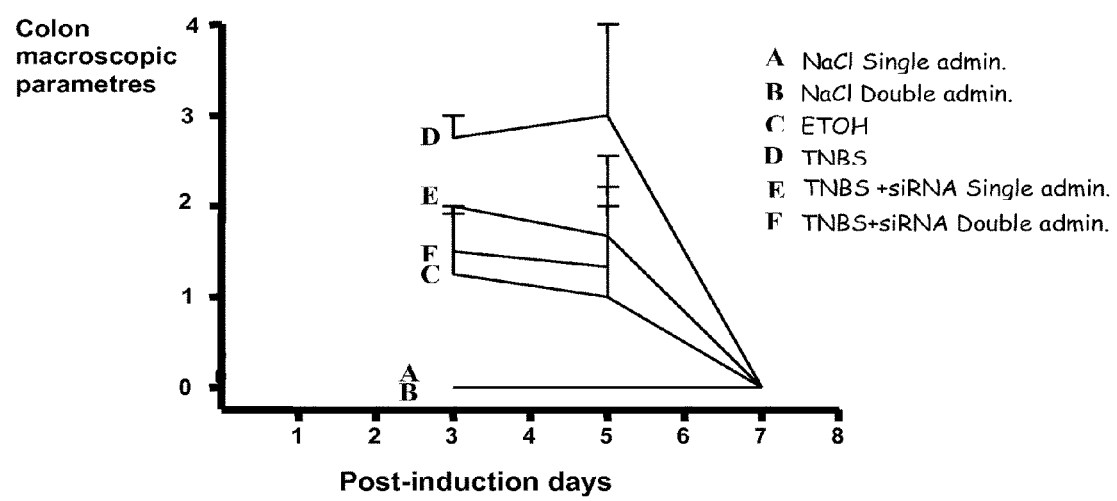
FIG. 12: Quantification of colon macroscopic parameters for each of the treatments described in the previous paragraph. Values were assigned ranging from 1 to 4, where 1 indicates no signs of colitis, and 4 indicates severe colitis.

Macroscopic observation of the colon at days 3, 5 and 7 in mice treated with TNBS showed an important shortening of the colon, accompanied by strong hyperemia, inflammation and necrosis, when compared to control animals (see FIG. 10). After IL-12p40 siRNA treatment recovery was observed in some individuals with respect to control animals at days 3 and 5, being more remarkable at day 5. At day 7 as also observed for other parameters, colon morphology was similar to that of controls. Both with one administration, where differences are more obvious, and with two administrations, a recovery is observed in terms of colon shortening and degree of inflammation, a remission of necrosis also being observed (see FIG. 12).

4. HYSTOPATHOLOGICAL ANALYSIS

Intrarectal application of NaCl does not affect colon morphology, and in ethanol controls one may observe slight lesions produced by the same. During the first days after colitis induction, inflammatory cell infiltrates were observed in colon mucosa and submucosa. On day 3 neutrophil transmural infiltration, a thinning of the colon, loss of goblet cells and ulcerations were observed. On day 5, loss of goblet cells is nearly complete and big disruptions of the epithelium may be observed, also an enormous submucosal infiltration of inflammatory cells and lymphocytes. After one administration of IL-12p40 siRNA, on day 3 no transmural lesions nor epithelium tearing is observed, although inflammatory cell infiltration of the submucosa is seen. Two administrations of IL-12p40 siRNA provoke, in some individuals, the loss of intestinal villi, whereas in other individuals villi integrity is maintained. In some examples, epithelium structure was preserved along with goblet cells, whereas in most cases affected loss of epithelial integrity was observed.

Figure 13:
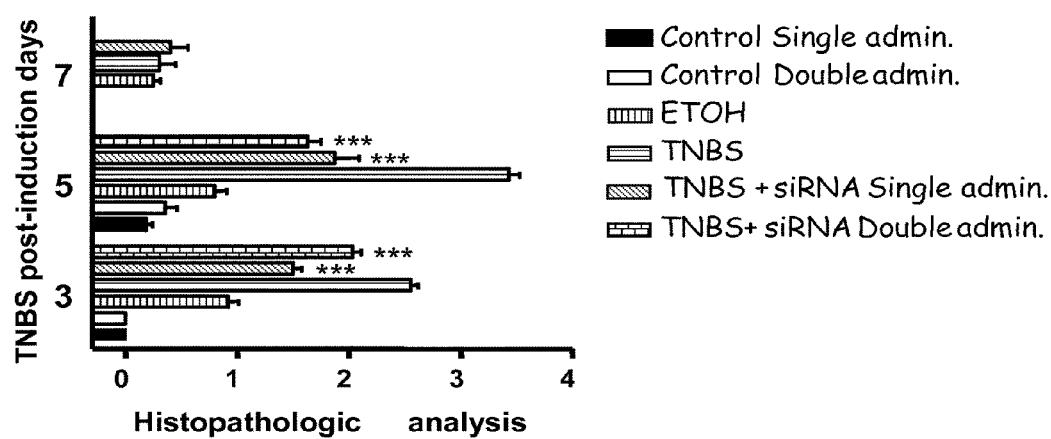
FIG. 13: Hystopathological analysis of colon samples from mice having received the treatments described in FIG. 11. Samples were 7 μm sections of colons obtained after whole organs were fixed, included and paraffin, stained using dyes described in the specification. For quantification purposes, the different stages were assigned numbers 0 to 4, wherein 0: no signs of inflammation, 1: scant leukocyte infiltration of lamina propria; 2: moderate leukocyte infiltration and some fibrosis; 3: high leukocyte infiltration, moderate fibrosis and loss of goblet cells; and 4: massive loss of goblet cells, extensive fibrosis, colon wall reduction and epithelium breakage.

On day 5 both one application of IL-12p40 siRNA and two applications produced very similar effects, wherein some individuals presented a histopathology reminiscent of TNBS treatment with loss of goblet cells, tearing of the epithelium and inflammatory cell infiltration, whereas other individuals had a more preserved morphology. As with other parameters, colon hystopathology was recovered 7 days after TNBS administration. These results are summarized in FIG. 13.

5. EVALUATION OF SERUM INFLAMMATORY PARAMETERS

Two important parameters of disease evolution, serum TNF-α and SAA, were also quantified.

TNFα plays a crucial role in all inflammatory processes and is also involved in the production of other important molecules that help the inflammatory process such as adhesion molecules and acute phase proteins, as well as other inflammatory mediators (nitric oxide, etc.)

Figure 14:
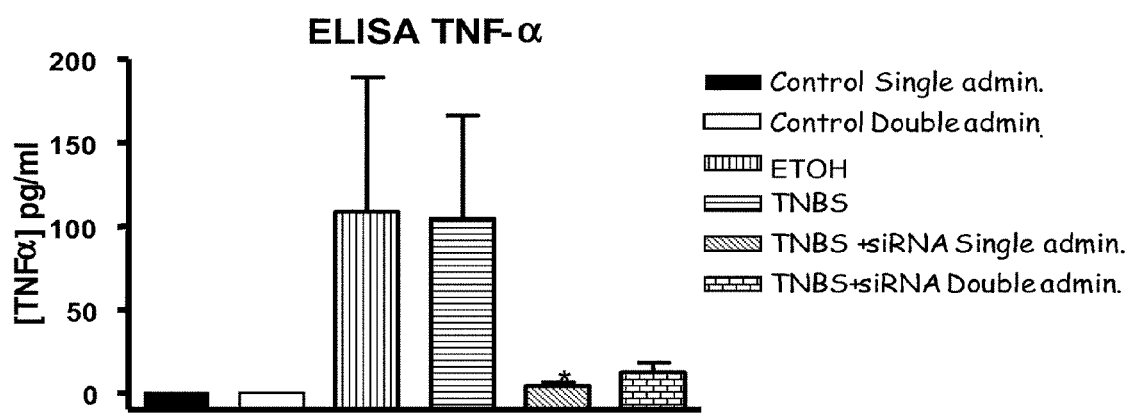
FIG. 14: ELISA test showing levels of Tumour Necrosis Factor-α in serum from animals having received treatments described in FIG. 11. Serum was extracted from blood samples obtained by cardiac puncture on days 3, 5 and 7 after TNBS administration.

After TNBS administration serum levels of TNFα underwent a drastic increase with respect to control individuals. 5 days after only one application of IL-12p40 siRNA a significant decrease of serum levels of TNFα was observed. Double administration reduced TNFα levels but differences were not significant with respect to TNBS administration. At day 5 no significant differences were observed between the groups and finally at day 7, TNFα levels were undetectable (see FIG. 14).

One of the factors directly involved in producing an acute inflammatory response is the production of hepatic acute phase proteins such as serum amyloid (SAA) whose levels are drastically increased during inflammation. Although during the first hours of inflammation it has a beneficial effect, the maintained inflammatory response produces the deposit of N-terminal peptides in small fibrils that are deposited in the kidney, liver and spleen producing lesions.

Figure 15:
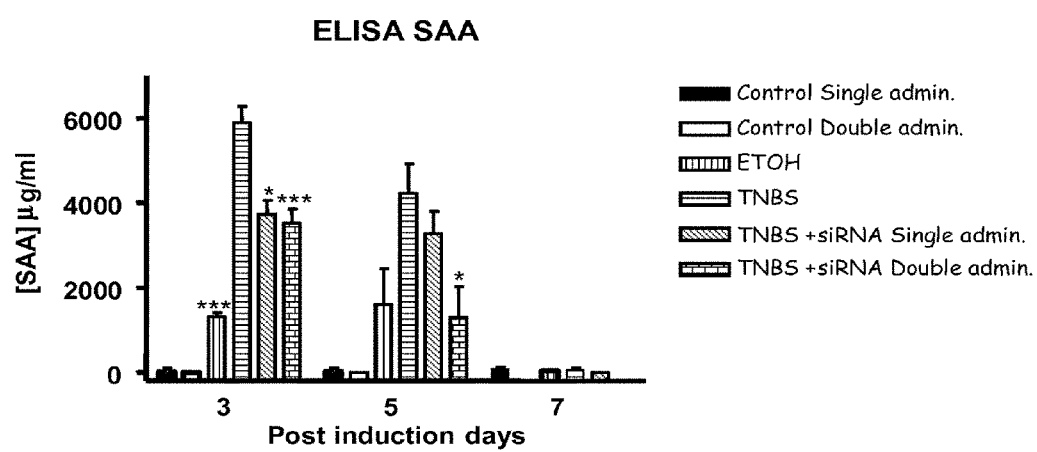
FIG. 15: ELISA test showing levels of Serum Amyloid A Protein (SAA) in serum from animals having received treatments described in FIG. 11. Serum was extracted from blood samples obtained by cardiac puncture on days 3, 5 and 7 after TNBS administration.

TNBS application produces an increase in the production of SAA of up to 6000 times compared to control values. Treatment with IL-12p40 siRNA produced at day 3, a significant decrease with one and two product administrations (see FIG. 15). At day 5 only the double product administration produced a significant decrease in serum SAA.

6. IL-12p40 mRNA EXPRESSION

Figure 17:
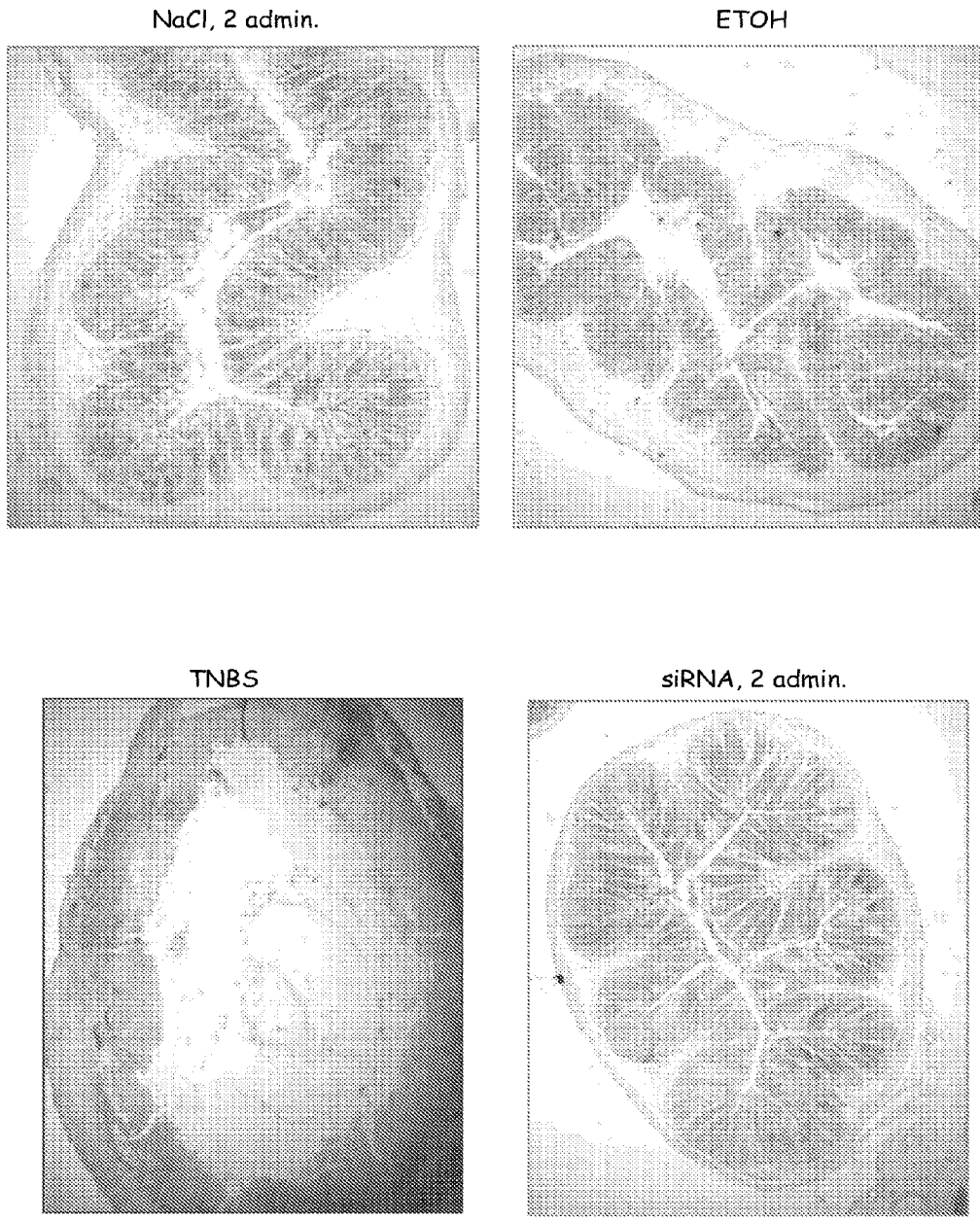
FIG. 17: Photographs of mice colon sections stained with ingrain blue/hemalum/picricindigocarmine Sections were obtained from mice 5 days after treatment with saline solution, ethanol, TNBS or TNBS plus 2 IL-12 specific siRNA administrations. Note loss of intestinal villi, general three-dimensional structure, and goblet cells in mice treated with TNBS alone, in comparison to the recovery observed in the colon of mice who had also received IL-12 specific siRNA.

On the other hand, IL12-p40 mRNA expression was measured in colon and mesenteric lymph node extracts, to check downregulation produced by the product. FIG. 16 shows how the increase of IL-12p40 mRNA induced by TNBS in the intestine, was significantly reduced by one or two applications of the product at days 3 and 5. Surprisingly, this mRNA reduction also took place at a peripheral level in the mesenteric lymph nodes, where on day 3 a significant reduction was observed with both applications when compared to TNBS (see FIG. 17).

7. CONCLUSION

In view of the above described results, one may conclude that IL-12p40 siRNA treatment has several beneficial effects on individuals suffering from Crohn's disease.

It is effective in extinguishing IL12-p40 signal expression both in the intestine and mesenteric lymph nodes. It reduces systemic manifestations of inflammation and acute phase such as circulating levels of serum amyloid and TNF, and it reduces the degree of intestinal hystopathological alterations.

Lastly, as it enhances survival of individuals in a very aggressive model for Crohn's disease.

The invention claimed is:

1. A pharmaceutical composition comprising a short interfering nucleic acid molecule (siNA) comprising a double-stranded nucleic acid region that has greater than 90% sequence identity or greater than 90% sequence complementarity with the entire contiguous length of SEQ ID NO: 67.

2. The pharmaceutical composition according to claim 1 wherein the siNA is selected from the group consisting of dsRNA, siRNA, and shRNA.

3. The pharmaceutical composition according to claim 2 wherein the siNA is siRNA.

4. The pharmaceutical composition according to claim 1 wherein the siNA comprises at least one modified oligonucleotide.

5. The pharmaceutical composition according to claim 1 wherein the siNA comprises at least one linkage between two nucleotides that is not a phosphodiester linkage.

6. The pharmaceutical composition according to claim 1, wherein the siNA is 40 nucleotides or less.

7. The pharmaceutical composition according to claim 1, wherein the siNA is double stranded over its entire length.

8. The pharmaceutical composition according to claim 1 wherein the siNA has a dinucleotide 3' overhang.

9. The pharmaceutical composition according to claim 8 wherein the dinucleotide overhang is made of thymidine nucleotides.

10. The pharmaceutical composition according to claim 1 wherein said siNA comprises a double-stranded nucleic acid region that has 100% sequence identity or 100% sequence complementarity with the entire contiguous length of SEQ ID NO: 67.

11. A short interfering nucleic acid molecule comprising the nucleic acid sequence of SEQ ID NO: 67.

* * * * *